(12) United States Patent
Crystal et al.

(10) Patent No.: US 12,031,144 B2
(45) Date of Patent: Jul. 9, 2024

(54) OXIDATION-RESISTANT AAT GENE THERAPY

(71) Applicant: Cornell University, Ithaca, NY (US)

(72) Inventors: Ronald G. Crystal, New York, NY (US); Katie Stiles, Bronx, NY (US); Meredith Sosulski, New York, NY (US); Stephen M. Kaminsky, Bronx, NY (US); Dolan Sondhi, New York, NY (US); Bishnu De, New Hyde Park, NY (US); Jonathan Rosenberg, Cranbury, NJ (US)

(73) Assignee: Cornell University, Ithaca, NY (US)

( * ) Notice: Subject to any disclaimer, the term of this patent is extended or adjusted under 35 U.S.C. 154(b) by 637 days.

(21) Appl. No.: 16/498,592

(22) PCT Filed: Mar. 29, 2018

(86) PCT No.: PCT/US2018/025183
§ 371 (c)(1),
(2) Date: Sep. 27, 2019

(87) PCT Pub. No.: WO2018/183705
PCT Pub. Date: Oct. 4, 2018

(65) Prior Publication Data
US 2020/0102575 A1     Apr. 2, 2020

Related U.S. Application Data

(60) Provisional application No. 62/478,357, filed on Mar. 29, 2017.

(51) Int. Cl.
*A61K 48/00* (2006.01)
*C12N 15/86* (2006.01)

(52) U.S. Cl.
CPC .............. *C12N 15/86* (2013.01); *A61K 48/00* (2013.01); *C12N 2750/14141* (2013.01)

(58) Field of Classification Search
CPC .... A61K 48/00; C12N 15/86; C12N 15/8645; C07K 14/8125
See application file for complete search history.

(56) References Cited

U.S. PATENT DOCUMENTS 4,711,848 A * 12/1987 Insley ................ C07K 14/8125
930/DIG. 530
4,973,668 A    11/1990 Jallat et al.
(Continued)

FOREIGN PATENT DOCUMENTS

FR    2599752 A1    12/1987
WO    WO-94/26896 A1    11/1994
(Continued)

OTHER PUBLICATIONS

Ferrarotti et al, Serum levels and genotype distribution of alpha1-antitrypsin in the general population, Thorax 67: 669-674, 2012.*
(Continued)

*Primary Examiner* — Kevin K Hill
(74) *Attorney, Agent, or Firm* — Schwegman Lundberg & Woessner, P.A.

(57) ABSTRACT

A gene therapy treatment for alpha 1-antitrypsin (AAT) deficiency is provided comprising a plasmid or viral, e.g., an AAV, vector coding for an elastase- or cathepsin G-inhibiting, oxidation-resistant human AAT with a substitution at, for example, Met358 and/or Met351.

19 Claims, 24 Drawing Sheets

- All of the candidate oxidant-resistant AAT variants generate AAT variants *in vivo* are effective inhibitors of neutrophil elastase in the context of oxidant stress, but the Val351Leu358 variant is the best inhibitor of cathepsin G with oxidant stress

(56) References Cited

U.S. PATENT DOCUMENTS

| | | | |
|---|---|---|---|
| 6,072,029 A * | 6/2000 | Courtney | A61P 43/00 530/808 |
| 8,980,266 B2 * | 3/2015 | Eckelman | A61P 17/06 530/391.1 |
| 9,574,192 B2 | 2/2017 | Sehgal et al. | |
| 2003/0152914 A1 * | 8/2003 | Kaplitt | C12N 15/86 435/235.1 |
| 2005/0106151 A1 | 5/2005 | Shapiro | |
| 2009/0203580 A1 | 8/2009 | Dinarello et al. | |
| 2011/0319330 A1 | 12/2011 | Shapiro | |
| 2012/0214747 A1 | 8/2012 | Brinkman et al. | |
| 2014/0371160 A1 | 12/2014 | Park et al. | |
| 2015/0079051 A1 | 3/2015 | Brunetti-Pierri et al. | |
| 2016/0186211 A1 * | 6/2016 | Flotte | A61K 48/0058 435/235.1 |

FOREIGN PATENT DOCUMENTS

| | | |
|---|---|---|
| WO | WO-2005048985 A2 | 6/2005 |
| WO | WO-2013/003641 A2 | 1/2013 |
| WO | WO-2016126857 A1 | 8/2016 |
| WO | WO-2018183705 A1 | 10/2018 |

OTHER PUBLICATIONS

Seixas et al, Known Mutations at the Cause of Alpha-1 Antitrypsin Deficiency an Updated Overview of SERPINA1 Variation Spectrum, Application of Clinical Genetics 14: 173-194, 2021.*

Ronzoni et al, The Importance of N186 in the Alpha-1-Antitrypsin Shutter Region Is Revealed by the Novel Bologna Deficiency Variant, Int. J. Mol. Sci. 22: e5668, 18 pages, doi.org/10.3390/ijms22115668, 2021.*

Renoux et al, Orphanet J. Rare Dis. 13: 7 pages, doi.org/10.1186/s13023-018-0897-0; available online Sep. 17, 2018.*

Wozniak et al, Challenges and Prospects for Alpha-1 Antitrypsin Deficiency Gene Therapy, Human Gene Therapy 26(11): 709-718, available online Aug. 5, 2015.*

De et al, Intrapleural administration of a serotype 5 adeno-associated virus coding for alpha1-antitrypsin mediates persistent, high lung and serum levels of alpha1-antitrypsin, Mol Ther 10(6):1003-1010, 2004.*

De et al, High Levels of Persistent Expression of A1-Antitrypsin Mediated by the Nonhuman Primate Serotype rh.10 Adeno-associated Virus Despite Preexisting Immunity to Common Human Adeno-associated Viruses, Mol. Ther. 13(1): 67-76, 2006.*

Chiuchiolo et al, Intrapleural Administration of an AAVrh.10 Vector Coding for Human a1-Antitrypsin for the Treatment of a1-Antitrypsin Deficiency, Human Gene Therapy Clinical Development 24: 161-173, 2013.*

Taggart et al, Oxidation of either Methionine 351 or Methionine 358 in a1-Antitrypsin Causes Loss of Anti-neutrophil Elastase Activity, J. Biol. Chem. 275(35): 27258-27265, 2000.*

McLean et al, Gene targeted therapeutics for liver disease in alpha-1 antitrypsin deficiency, Biologics: Targets & Therapy 3: 63-75, 2009.*

Shahin et al, Pulmonary function tests, high-resolution computerized tomography, α1-antitrypsin measurement, and early detection of pulmonary involvement in patients with systemic sclerosis, Rheumatology Int. 20: 95-100, 2001.*

Herzog et al, Interstitial Lung Disease Associated With Systemic Sclerosis and Idiopathic Pulmonary Fibrosis, Arthritis Rheumatol. 66(8): 1967-1978, 2014.*

Fregonese et al, Alpha-1 antitrypsin Null mutations and severity of emphysema, Respiratory Medicine 102: 876-884, 2008.*

Al-Bayaty et al, The Influence of Cigarette Smoking on Gingival Bleeding and Serum Concentrations of Haptoglobin and Alpha 1-Antitrypsin, BioMed Res. Int'l, Article ID 684154, doi.org/10.1155/2013/684154, 6 pages, 2013.* en.wikipedia.org/wiki/Mammal, last visited Aug. 31, 2022.*

Courtney et al, The construction of novel protease inhibitors by modification of the active centre of alpha1-antitrypsin, Philosophical Transactions of the Royal Society A: Mathematical, Physical and Engineering Sciences, doi.org/10.1098/rsta.1986.0048; 1986; (Abstract only).*

Jallat et al, Antiprotease targeting: altered specificity of α-antitrypsin by amino acid replacement at the reactive centre, Revue Française de Transfusion et Immuno-hématologie, 29(4): 287-298, 1986 (Abstract only).*

"European Application Serial No. 18777905.3, Extended European Search Report dated Dec. 3, 2020", 7 pgs.

Crystal, R. G., et al., "The alpha 1-antitrypsin gene and its deficiency states", Trends In Genetics, vol. 5, (Jan. 1, 1989), 411-417.

"International Application Serial No. PCT/US2018/025183, International Search Report dated Jun. 26, 2018", 3 pgs.

"International Application Serial No. PCT/US2018/025183, Written Opinion dated Jun. 26, 2018", 7 pgs.

Chiuchiolo, Maria J., et al., "Gene Therapy for Alpha-1 Antitrypsin Deficiency Lung Disease", AnnalsATS vol. 13 Supplemental 4 / Aug. 2016, Department of Genetic Medicine, Weill Cornell Medical College, New York, New York, (Aug. 2016), S352-S369.

Janoff, Aaron, et al., "A genetically engineered, mutant human alpha-1-proteinase inhibitor is more resistant than the normal inhibitor to oxidative inactivation by chemicals, enzymes, cells, and cigarette smoke", Am Rev Respir Dis., 133(3), (1986), 353-356.

Jha, Shweta, et al., "Single amino acid substitutions in recombinant plant-derived human a1-proteinase inhibitor confer enhanced stability and functional efficacy", Biochimica et Biophysica Acta (BBA)—General Subjects, 1840(1), (416-427), Jan. 2014.

Luisetti, Maurizio, et al., "Bioengineering: alpha sub1-Proteinase Inhibitor Site-Specific Mutagenesis", Chest, 110, (1996), 278S-283S.

McLean, Caitriona, et al., "Gene targeted therapeutics for liver disease in alpha-1 antitrypsin de? ciency", Biologics: Targets & Therapy, 3, (2009), 63-75.

Ray, Bimal K., et al., "Expression and Structural Analysis of a Novel Highly Inducible Gene Encoding alpha sub 1-Antitrypsin in Rabbit", The Journal of Biological Chemistry, 269(35), (1994), 22080-22086.

Rosenberg, Steven, et al., "Synthesis in yeast of a functional oxidation-resistant mutant of human alpha sub 1-antitrysin", Nature, 312, (1984), 77-80.

Silberstein, David Z., et al., "115—Plant-Based Production, Purification, and Characterization of Oxidation-Resistant Alpha-1 Antitrypsin", Free Radical Biology and Medicine, vol. 100, Supplement, Science Direct, (Nov. 2016), S59-S60.

Silberstein, David, et al., "Production and Preliminary In Vitro Evaluation of a Plant-Made, Oxidation Resistant Alpha-1 Antitrypsin", American Journal of Respiratory and Critical Care Medicine, 195, A2429, (2017), 1 pg.

Taggart, et al., "Oxidation of either methionine 351 or methionine 358 in alpha 1-antitrypsin causes loss of anti-neutrophil elastase activity", Journal of Biological Chemistry, vol. 275, Iss. 35, (Jun. 23, 2000), 27258-27265.

"International Application Serial No. PCT/US2018/025183, International Preliminary Report on Patentability dated Oct. 10, 2019", 8 pgs.

Radojkovic, Dragica, "Chapter 2—Polymerization and Oxidation of Alpha-1-Antitrypsin in Pathogenesis of Emphysema", [online]. Retrieved from the Internet: <URL: https://www.intechopen.com/books/lung-diseases-selected-state-of-the-art-reviews/polymerization-and-oxidation-of-alpha-1-antitrypsin-in-pathogenesis-of-emphysema>, (Mar. 2012), 55-82.

"European Application Serial No. 18777905.3, Response filed Jun. 29, 2021 to Extended European Search Report dated Dec. 3, 2020", 7 pgs.

"European Application Serial No. 18777905.3, Communication Pursuant to Article 94(3) EPC dated Oct. 26, 2022", 5 pgs.

"European Application Serial No. 18777905.3, Response Filed Mar. 3, 2023 to Communication Pursuant to Article 94(3) EPC dated Oct. 26, 2022", 7 pgs.

(56) References Cited

OTHER PUBLICATIONS

Chakraborti, Sajal, et al., "Role of Proteases in Lung Disease: A Brief Overview", Springer Nature Singapore Pte Ltd., S. Chakraborti et al. (eds.) Proteases in Human Diseases, DOI 10.1007/978-981-10-3162-5_16, Department of Biochemistry and Biophysics, University of Kalyani, Kalyani 741235, West Bengal, India, (2017), 333-374.
Chiuchiolo, Maria, et al., "Gene Therapy for Alpha-1 Antitrypsin Deficiency Lung Disease", Am Thorac Soc vol. 13, Supplement 4, pp. S352-S369, Aug. 2016, (Aug. 2016), 18 pgs.
Sosulski, Meredith L., et al., "Gene therapy for alpha 1-antitrypsin deficiency with an oxidantresistant human alpha 1-antitrypsin", JCI Insight. 2020;5(15):e135951., (Aug. 6, 2020), 17 pgs.
Stiles, Katie, et al., "Intrapleural Gene Therapy for Alpha-1 Antitrypsin Deficiency-Related Lung Disease", Chronic Obstr Pulm Dis. 2018;5(4):244-257., (Jan. 15, 2018), 14 pgs.

\* cited by examiner

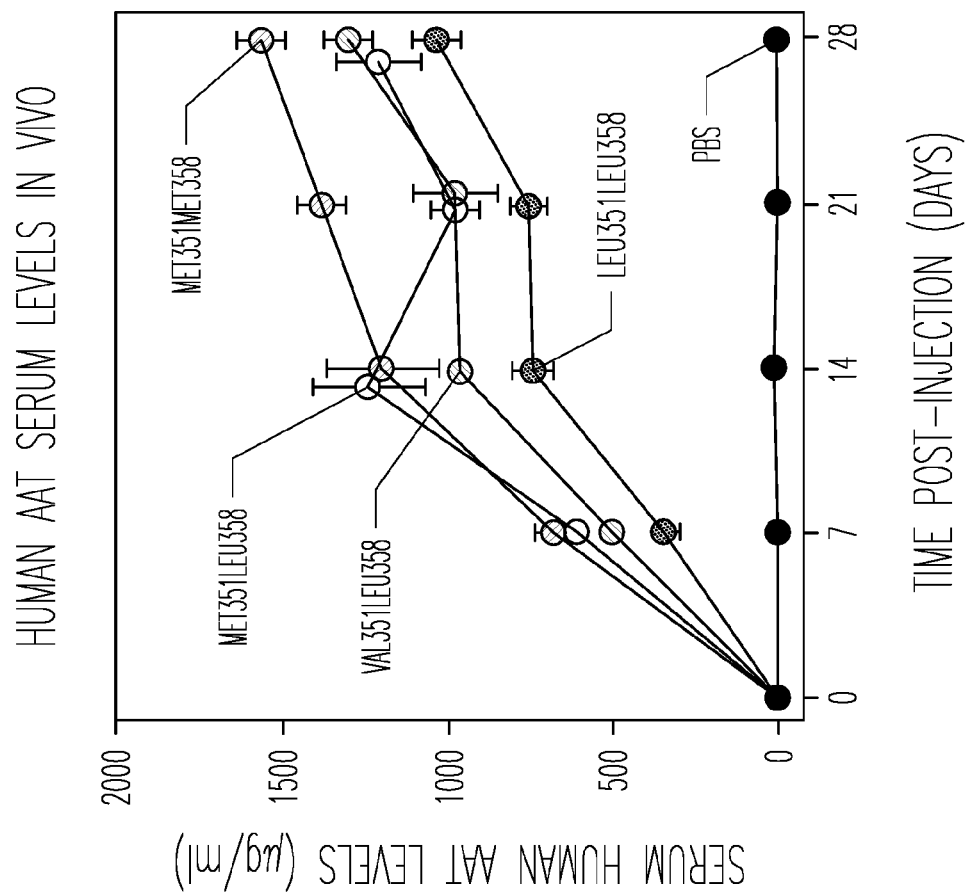
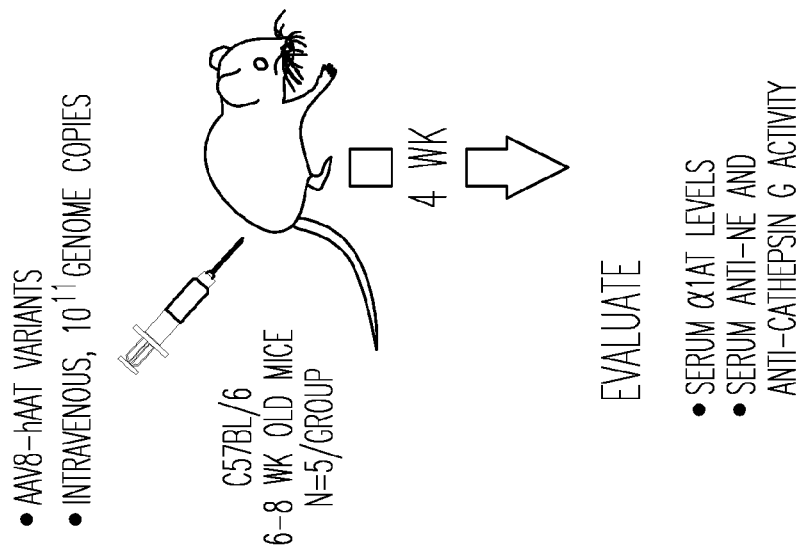
Fig. 15

- All of the 2nd generation oxidant-resistant AAT variants expressed in serum *in vivo* are effective inhibitors of neutrophil elastase and cathepsin G

- All of the candidate oxidant-resistant AAT variants in vivo are effective inhibitors of neutrophil elastase in the context of oxidant stress, but the Val351Leu358 variant is the best inhibitor of cathepsin G with oxidant stress

OXIDATION-RESISTANT AAT GENE THERAPY

CROSS-REFERENCE TO RELATED APPLICATIONS

This application is a U.S. national state filing under 35 U.S.C. 371 from International Application No. PCT/US2018/025183, filed on 29 Mar. 2018, and published as WO 2018/183705 on 4 Oct. 2018, which claims the benefit of the filing date of U.S. application Ser. No. 62/478,357, filed on Mar. 29, 2017, the disclosures of which are incorporated by reference herein.

BACKGROUND

AAT, (SERPINA1), a 52 kDa a serum serine protease inhibitor, functions to protect the lung from the powerful protease neutrophil elastase (NE)[4-10]. AAT also inhibits the activity of other neutrophil-released proteases, including proteinase 3, α-defensins and cathepsin G and has anti-inflammatory and immunomodulatory properties[48-88]. Serum deficiency of AAT is associated with an imbalance between proteases and AAT in the lung, leading to slow destruction of the lung parenchyma, a process accelerated by cigarette smoking[4,5,7,8,11,12,59-61]. The consequence is the development of early-onset of panacinar emphysema at ages 35 to 40 in smokers and age 55 to 60 in nonsmokers, with a reduced life span of approximately 15 to 20 yr[4,57,32-64] The disorder affects 70,000 to 100,000 individuals in the USA[82,88]. AAT deficiency is also associated with childhood and adult liver cirrhosis, and rarely with hepatocellular carcinoma, panniculitis and vasculitis and autoimmune disorders[66-73]. AAT is mainly produced in the liver reaching the lung by diffusion from the circulation[4,5,7,8,10-12,63,74] with a small percentage secreted from mononuclear phagocytes[78,78], neutrophils[77], bronchial epithelial cells[78,79], and small intestine epithelial cells[80,81]. AAT in plasma diffuses into the lung, where it protects the fragile alveolar structures from proteases carried by neutrophils generated in bone marrow. The lung is the organ most susceptible to neutrophil elastase mediated proteolytic destruction (FIG. 1).

Low circulating levels of AAT are the result of mutations in the SERPINA1 gene (MIM 107400)[82,83], with more than 120 naturally occurring alleles[88,84-88]. The normal AAT alleles are M1(Ala213), M1(Val213), M2, M2 and M4[87]. The most common deficient variants are the severe Z allele, observed with high frequency in Caucasians in Northern European countries and North America, and the milder S form, with high prevalence in the Iberian Peninsula[65,70,88]. The vast majority of cases of emphysema associated with AAT deficiency are caused by homozygous inheritance of the severe Z variant, with a single amino acid substitution of lysine for glutamic acid at position 342 (E342K)[88]. The Z mutation causes the AAT protein to polymerize in hepatocytes, preventing secretion into the blood[83,88,70,88-92]. The S allele, a single amino acid substitution of a glutamic acid by a valine at position 264 (E264V), results in an unstable protein with reduced serum half-life[93-98]. Individuals homozygous for the Z mutation (ZZ) have plasma AAT levels 10 to 15% of the normal M allele and account for approximately >95% of cases of clinically recognized AAT deficiency[5,7,10,11,65,71,97].

SUMMARY

Gene therapy vectors comprising an expression cassette coding for an oxidation-resistant alpha 1-antitrypsin (AAT) are provided. The oxidation-resistant alpha 1-antitrypsin nucleic acid may comprise one or mutations encoding one or more substitution(s), e.g., those described in Table 1, and the resulting AAT protein (a variant relative to the parental AAT sequence) is oxidation-resistant compared to an AAT sequence that does not have the one or more substitutions (e.g., the parental AAT nucleic acid sequence made encode an oxidation-sensitive AAT sequence, such as a M1(Ala213) sequence). Thus, in one embodiment, the base expression cassette that encodes an oxidation-sensitive AAT that is then made oxidation-resistant, may be the M1(Ala213) variant. In another embodiment, the base expression cassette that encodes an oxidation-sensitive AAT that is then made oxidation-resistant may be the M1(Val213) variant. Also provided are methods to treat alpha 1-antitrypsin deficiency comprising administering to a subject in need thereof, a pharmaceutical composition comprising one or more vectors described herein. In one embodiment, the vector may be delivered to the pleura. In one embodiment, the vector may be intravenously delivered Advantages of gene therapy include that 1) a single administration may permanently compensate for the genetic abnormality, obviating the requirement of weekly or monthly parenteral infusions of AAT, 2) a steady state of AAT occurs over time, 3) there is a lack of risk of viral contamination from pooled plasma, and 4) there may be a lower cost.

In one embodiment, a viral or plasmid gene therapy vector is provided comprising an expression cassette coding for an oxidation-resistant alpha 1-antitrypsin that has an oxidation-resistant amino acid at, for example, position 351, position 358, or both positions 351 and 358. In one embodiment, the oxidation-resistant amino acid is leucine, valine, glycine, isoleucine, alanine, threonine, asparagine, serine, or aspartic acid. In one embodiment, the oxidation-resistant amino acid is leucine, valine, glycine, isoleucine, or alanine. In one embodiment, position 358 in alpha 1-antitrypsin has an oxidation-resistant amino acid. In one embodiment, position 351 has an oxidation-resistant amino acid. In one embodiment, position 358 has an oxidation-resistant amino acid. In one embodiment, position 351 and position 358 each has an oxidation-resistant amino acid. In one embodiment, the oxidation-resistant residue is leucine or valine. In one embodiment, the alpha 1-antitrypsin has an alanine at position 213. In one embodiment, the alpha 1-antitrypsin sequence other than the residue at position 351 and/or 358 is the M1(Ala213) variant sequence. In one embodiment, the alpha 1-antitrypsin has a valine at position 213. In one embodiment, the alpha 1-antitrypsin sequence other than the residue at positions 351 and/or 358 is the M1 (Val213) variant sequence. In one embodiment, the vector is a viral gene therapy vector, e.g., an adenovirus, adeno-associated virus (AAV), retrovirus or lentivirus vector. In one embodiment, the AAV vector is pseudotyped. In one embodiment, the AAV vector is pseudotyped with AAVrh.10, AAV8, AAV9, AAV5, AAVhu.37, AAVhu.20, AAVhu.43, AAVhu.8, AAVhu.2, or AAV7 capsid. In one embodiment, the AAV vector is pseudotyped with AAVrh.10, AAV8, or AAV5. In one embodiment, the AAV vector is AAV2, AAV5, AAV7, AAV8, AAV9 or AAVrh.10. Further provided is a pharmaceutical composition comprising an amount of the gene therapy vector described above. A dose of the viral vector may be about $1 \times 10^{11}$ to about $1 \times 10^{16}$ genome copies, about $1 \times 10^{12}$ to about $1 \times 10^{15}$ genome copies about $1 \times 10^{11}$ to about $1 \times 10^{13}$ genome copies, or about $1 \times 10^{13}$ to about $1 \times 10^{15}$ genome copies.

The vector or pharmaceutical composition may be employed to prevent, inhibit or treat alpha 1-antitrypsin deficiency. For example, an effective amount of the vector or the pharmaceutical composition may be administered to a subject in need thereof. In one embodiment, the composition is delivered to the pleura. In one embodiment, the composition is intravenously administered. In one embodiment, the subject is a human. In one embodiment, the human has emphysema.

The vector or pharmaceutical composition may also be employed to prevent, inhibit or treat emphysema, COPD, respiratory distress syndrome or fibrotic interstitial lung disease in a mammal by administering to a mammal in need thereof, an effective amount of the vector or the pharmaceutical composition. In one embodiment, the composition is delivered to the pleura. In one embodiment, the composition is intravenously administered. In one embodiment, the mammal is a human. In one embodiment, the human has emphysema.

The vector or pharmaceutical composition may further be employed to prevent, inhibit or treat oxidative damage to the lung, e.g., by administering to a subject in need thereof an effective amount of a composition comprising the vector or the pharmaceutical composition. In one embodiment, the composition is delivered to the pleura. In one embodiment, the composition is intravenously administered. In one embodiment, the subject is a human.

BRIEF DESCRIPTION OF THE DRAWINGS

FIG. 15. Evaluation of AAV8-hAAT variants in a mouse model.

DETAILED DESCRIPTION

Figure 1:
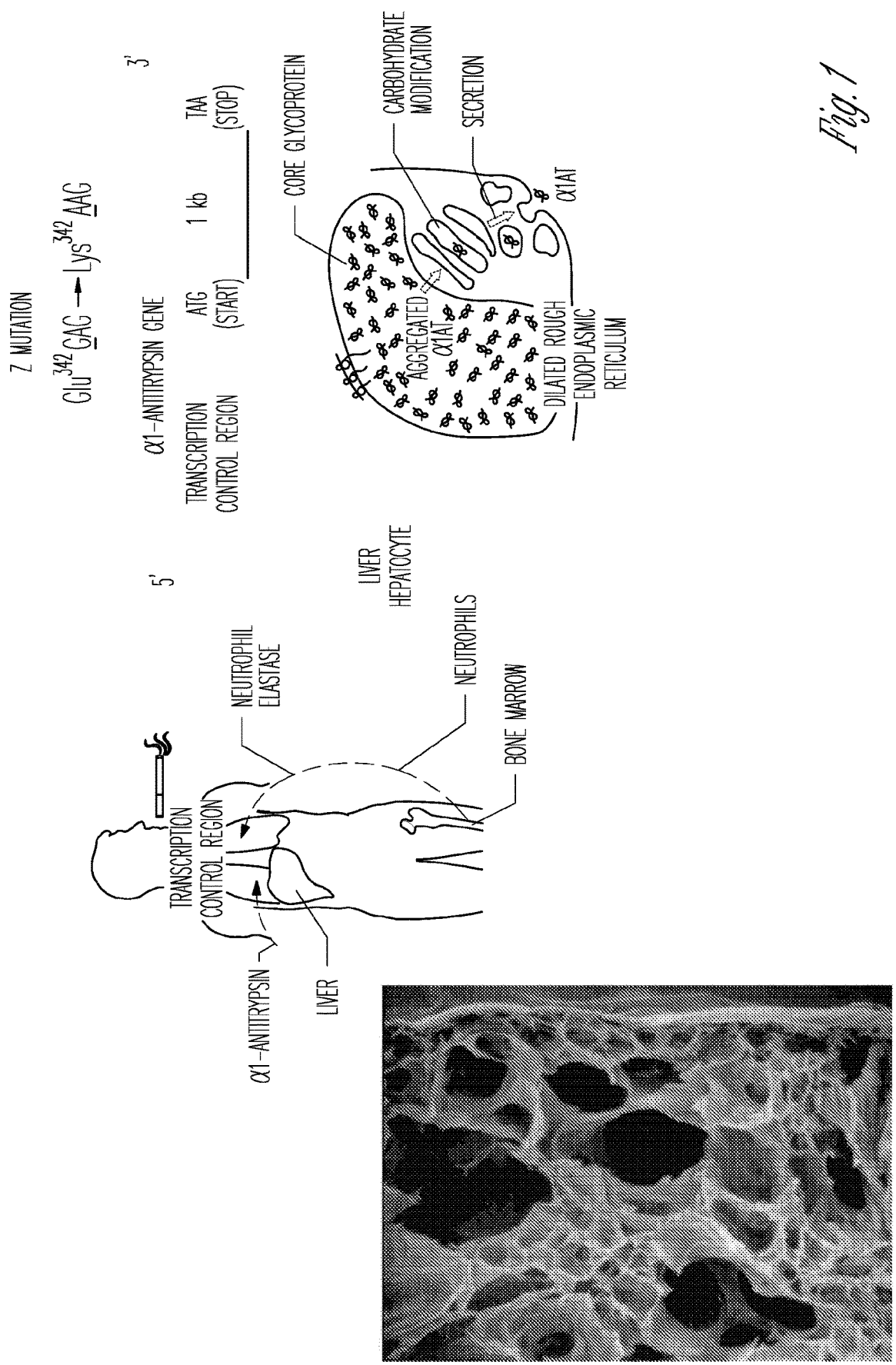
FIG. 1. Pathogenesis of AAT deficiency. Left. AAT produced in the liver functions to protect the lung from the burden of neutrophil elastase. Middle. With the Z mutation in the AAT gene, the AATZ protein aggregates in the liver resulting in low AAT levels in blood and hence lung. Bottom. The consequence is progressive lung destruction resulting in emphysema (scanning EM).

In the following description, reference is made to the accompanying drawings that form a part hereof, and in which is shown byway of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Definitions

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered; sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well know n to the art including, but not limited to, protein expression (including steady state levels), e.g.; by ELISA, flow cytometry and Western blot, measurement of DNA and RNA by hybridization assays, e.g., Northern blots, Southern blots and gel shift mobility assays. Methods used for the introduction of the exogenous polynucleotide include well-know n techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms know nor predicted to make up the double-stranded form.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded), Enrichment can be measured on an absolute basis, such as weight per volume of solution, or it can be measured in relation to a second, potentially interfering substance present in the source mixture. Increasing enrichments of the embodiments of this invention are increasingly preferred. Thus, for example, a 2-fold enrichment, 10-fold enrichment, 100-fold enrichment, or a 1000-fold enrichment.

A "transcriptional regulatory sequence" refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular; as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specifics termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, such as mammalian cells including human cells, useful in the present invention; e.g.; to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements know n in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as w ell as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are know n and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably; two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g.; 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size); and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

"Conservative" amino acid substitutions are, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine; alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine; arginine, and histidine; and a group of amino acids having sulfur-containing side chains is cysteine and methionine. For example, it is reasonable to expect that replacement of a leucine with an isoleucine or valine, an aspartate with a glutamate; a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide. Naturally occurring residues are divided into groups based on common side-chain properties: (1) hydrophobic: norleucine, met, ala; val, leu, ile; (2) neutral hydrophilic: cys, ser, thr; (3) acidic; asp, glu; (4) basic; asn, gin, his, lys, arg; (5) residues that influence chain orientation: gly, pro; and (6) aromatic; trp, tyr, phe. The invention also envisions polypeptides with non-conservative substitutions. Non-conservative substitutions entail exchanging a member of one of the classes described above for another.

Nucleic Acid Sequence which Encodes an AAT

AAT, (SERPINA 1), a 52 kDa a serum serine protease inhibitor; functions to protect the lung from the powerful protease neutrophil elastase (NE)[4-10] Low circulating levels of AAT are the result of mutations in the SERPINA 1 gene (MIM 107400)[82,83]; with more than 120 naturally occurring alleles[65,84-86]. The normal AAT alleles are M1 (Ala213), M1(Val213), M2, M2 and me. The most common deficient variants are the severe Z allele, observed with high frequency in Caucasians in Northern European countries and North America, and the milder S form, with high prevalence in the Iberian Peninsula[65,70,85]. AAT deficiency is a common, fatal autosomal recessive disorder characterized by low (<11 µM) plasma levels of AAT. Generally; is it associated with the development of panacinar emphysema, manifesting clinically in smokers ages 35-45 and in nonsmokers 55-65. Current therapy is weekly or monthly intravenous administration of AAT purified pooled plasma.

The vast majority of cases of emphysema associated with AAT deficiency are caused by homozygous inheritance of the severe Z variant; with a single amino acid substitution of lysine for glutamic acid at position 342 (E3421c)[88]. The Z mutation causes the AAT protein to polymerize in hepatocytes, preventing secretion into the blood[63,65,70,88-92]. The S allele, a single amino acid substitution of a glutamic acid by a valine at position 264 (E264V), results in an unstable protein with reduced serum half-life[93-96]. Individuals homozygous for the Z mutation (ZZ) have plasma AAT levels 10 to 15% of the normal M allele and account for approximately >95% of cases of clinically recognized AAT deficiency[5,7,10,11,65,71,97].

An exemplary adeno-associated virus, e.g., serotype 8 adeno-associated virus, was prepared for coding for a next generation oxidation-resistant AAT in vivo gene therapy strategy to treat the pulmonary manifestations of AAT deficiency. Throughout this specification which includes its figures, an embodiment is at times referenced as AAV.vAAT.

A significant advantage of the compositions provided herein is that they provide an oxidation-resistant form of AAT that provides a more stable, effective therapy, despite the persistent stress of the AAT in the lung by inhaled oxidants; common in everyday life[101,102] this regard, compositions described herein have the marked advantage in that, for the amount of AAT available to defend the lower respiratory tract, AAV.vAAT is far more likely to make available functional AAT molecules to defend the alveolar structures from NE, requiring less gene therapy-generated AAT to be effective.

Compositions

The parameters relevant to designing the composition include: (1) the viral vector or capsid; (2) the expression cassette including the promoter and AAT coding sequence; and (3) route of administration.

Capsid.

Figure 2A:
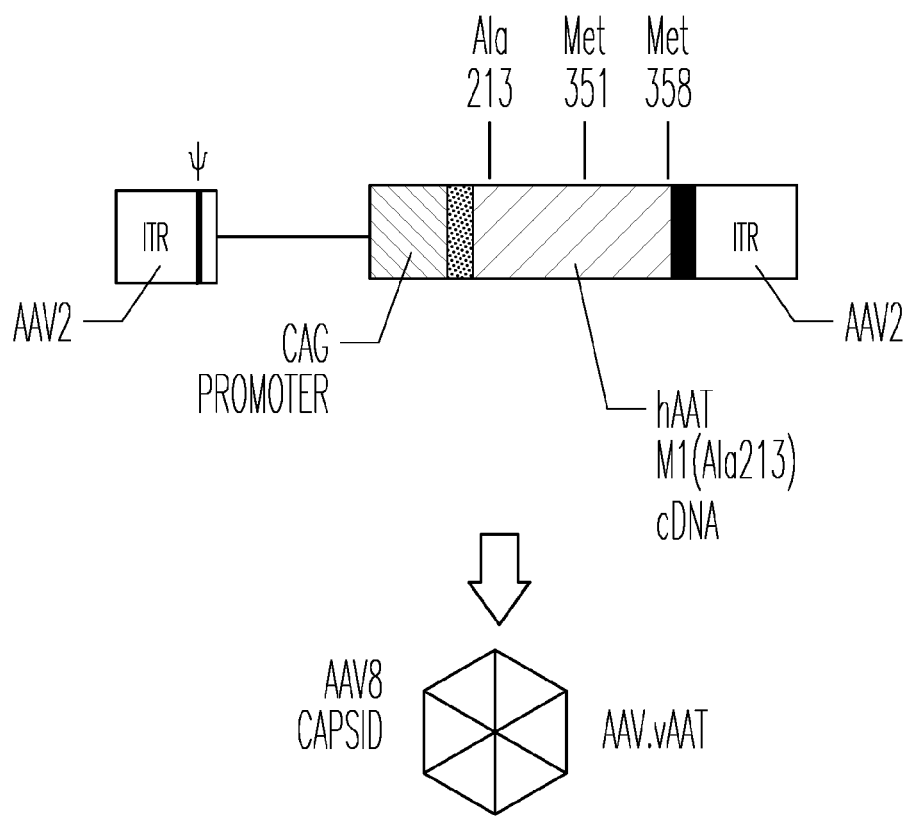
FIGS. 2A-D. Composition. A) Structure of an embodiment, based on the serotype AAV8 vector. Show n in the expression cassette is the coding sequence for the AAT cDNA driven by the highly active, constitutive CAG promoter, followed by an intron, the RAT cDNA and the polyA signal flanked by AAV2 inverted terminal repeats (ITR), Indicated are the AAT cDNA is A213, and the 2 Met sites to be varied with Leu and/or Val. The genome is packaged in an AAV8 capsid. B) Crystallographic structure of the normal AAT M1(Ala213) protein (adapted from PDB 1QLP)[120]. AAT protects the lung from serine proteases capable of degrading the lung parenchyma. Oxidation of Met358 and Met 351 in the AAT active site renders AAT incapable of inhibiting elastase and cathepsin G. In human, oxidants in cigarette smoke, second hand smoke and pollutants oxidize and inactivate AAT, rendering the lung at risk for protease-mediated destruction. C) Evolution of the human AAT gene. There are 5 major normal AAT variants, M1(A213), M1 (V213), M2, M3 and M4. M2 could be from M3 or M4. Based on the know ledge that the common Z allele (>95% cases of AAT deficiency) is derived from the M1 (A213) normal AAT allele, AAV.vAAT is based on the M1(Ala213) base sequence.

AAV is highly effective in transducing organs in vivo, with persistent expression[103,106]. AAV is a small parvovirus that does not cause human disease. There are 6 human serotypes and >50 nonhuman serotypes, primarily from nonhuman primates[107]. The most effective, and most commonly used AAV vectors are serotypes 1,2,5,8,9 and rh.10[108]. As detailed in 4. Approach, based on evaluation of 25 serotypes, the AAV8 vector was effective in generating high, persistent levels of human AAT in experimental animals. In an embodiment, the composition comprises the AAV8 capsid with a genome that includes the highly active CAG promoter[109], an artificial intron, the oxidation resistant human AAT cDNA (described below) and polyA signal (FIG. 2A).

Expression Cassette.

Figure 2B:
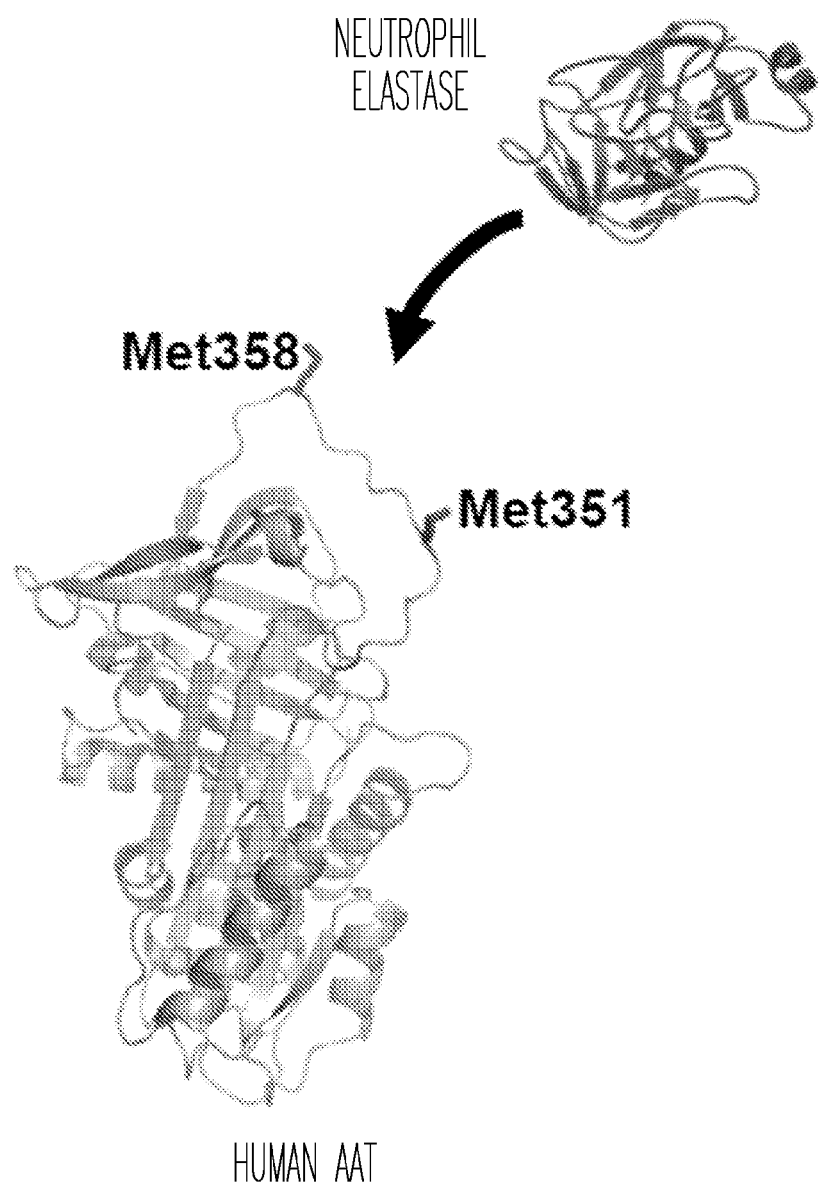
Figure 2C:
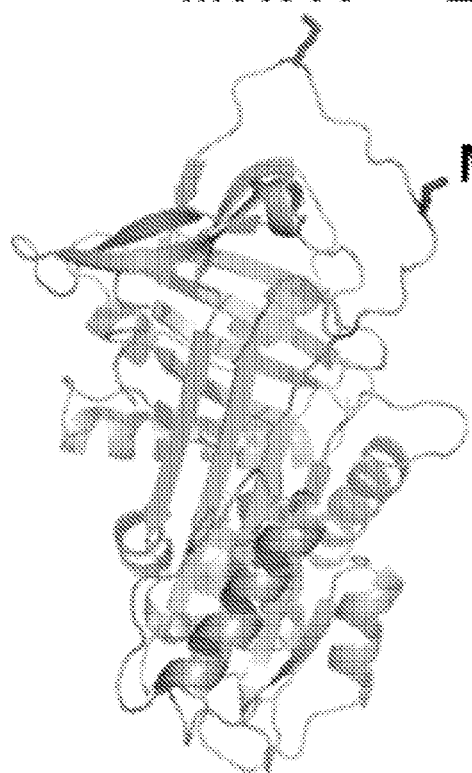
Figure 2D:
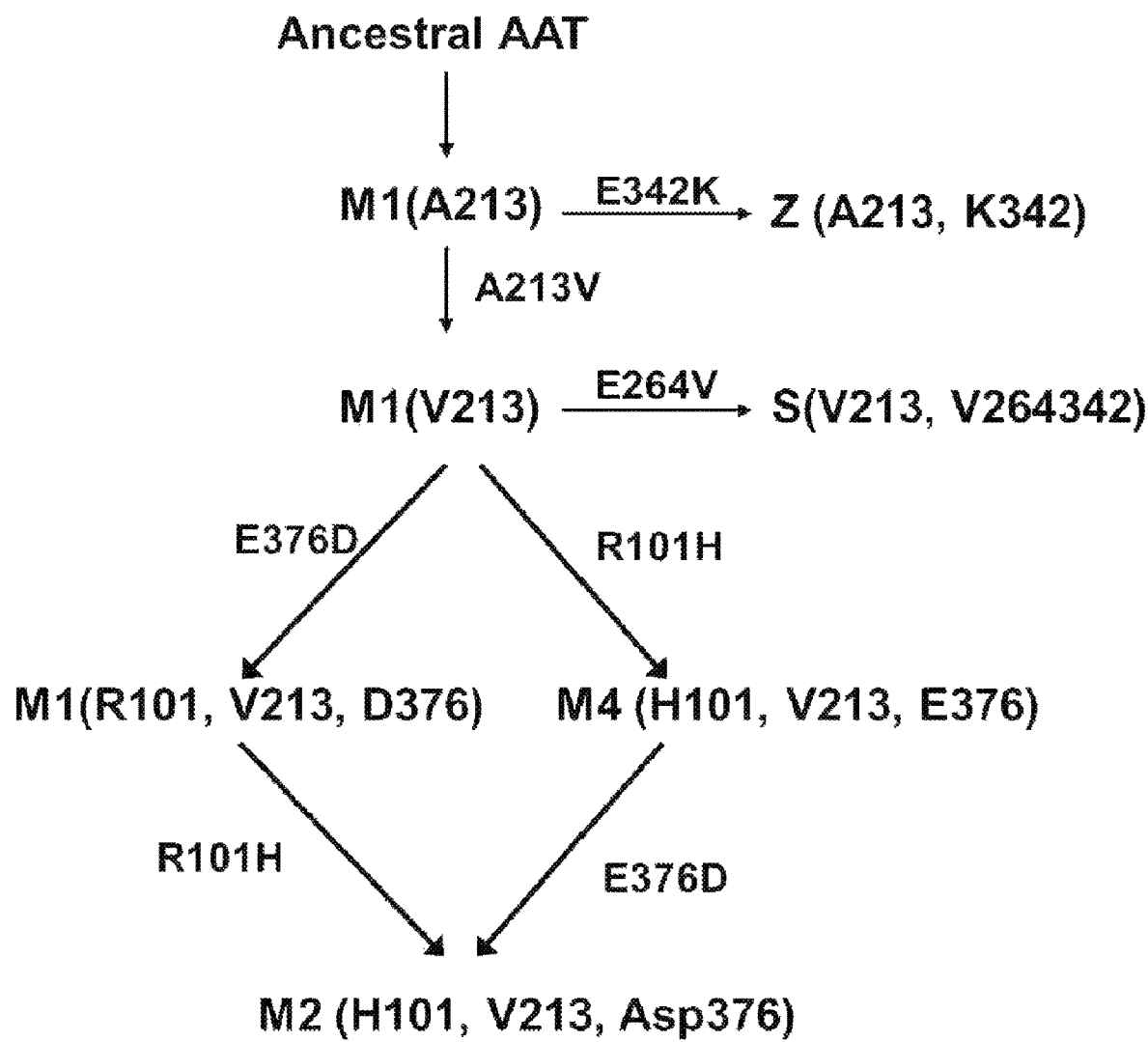
Figure 3:
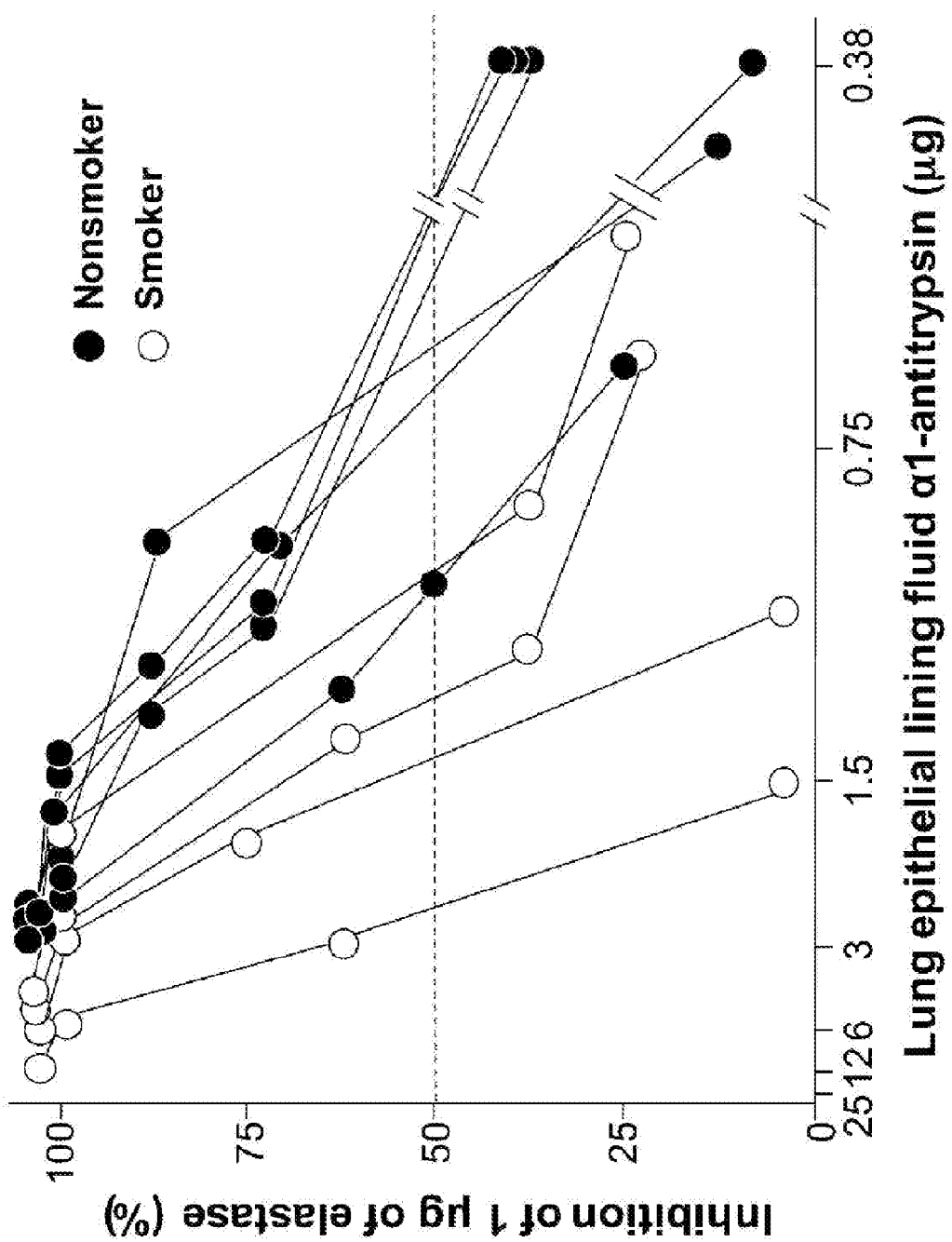
FIG. 3. Elastase inhibitory activity in fluid from the epithelial surface of the lower respiratory tract of smoking and nonsmoking individuals. ELF was obtained by inserting a fiberoptic bronchoscope into a segmental bronchus. Five 20 ml portions of physiologic saline were injected through the bronchoscope; the lay age fluid was collected in a sterile vial by aspiration, separated from the cells by centrifugation at 500 g for 5 min, and concentrated by pressure dialysis (Amicon UM2 membrane) to a volume of 1 ml. The amount of AAT in each lavage sample was determined and elastase inhibitory activity of the lavage samples was measured[121]. Shown is AAT from the epithelial lining fluid of nonsmokers (●) and smokers (○).
Figures 4A, 4B:
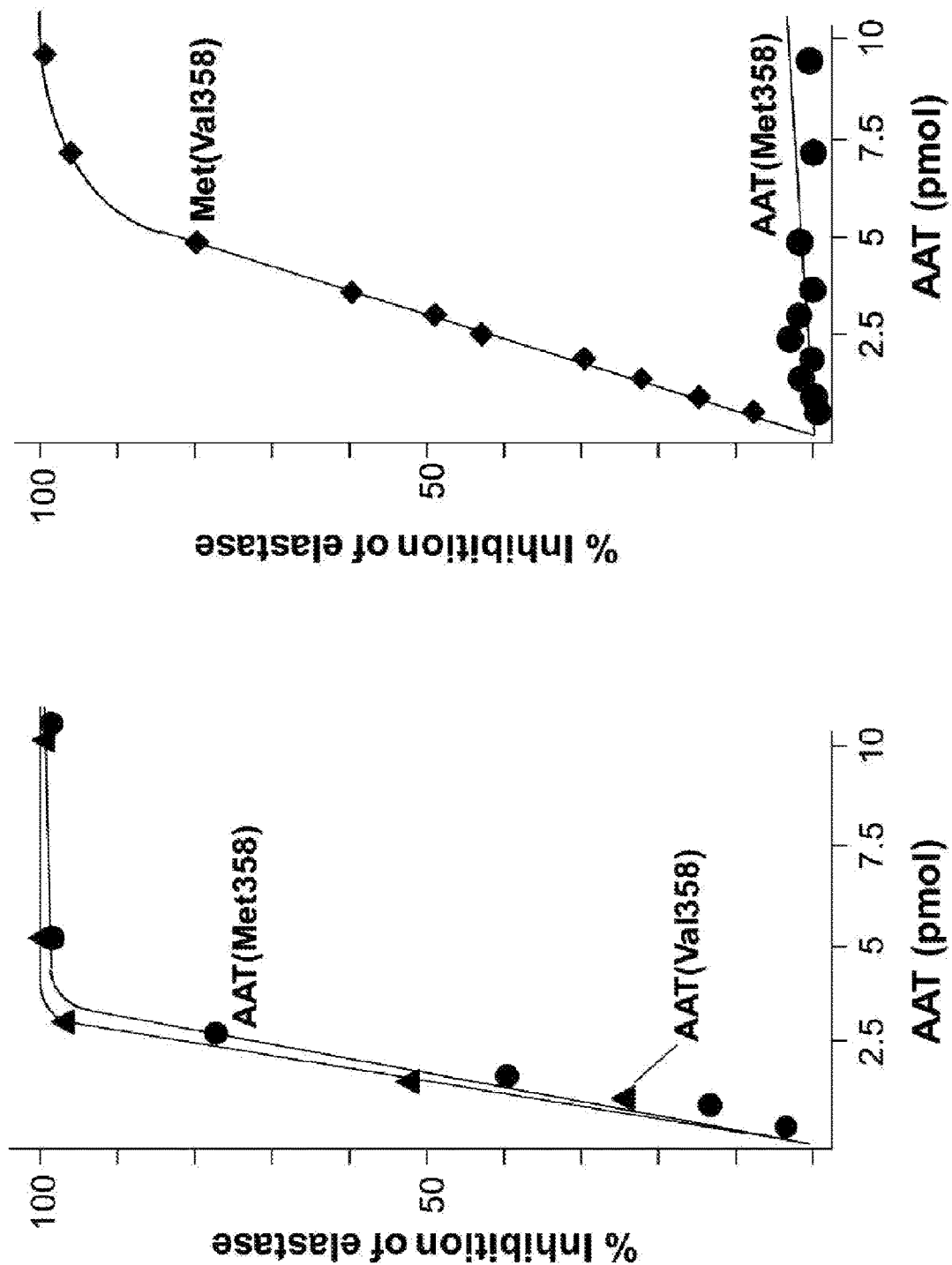
FIGS. 4A-B. Inhibition of elastase by AAT(Met358) and AAT(Val358) in the absence and presence of oxidation. A) Inhibition of human neutrophil elastase with AAT(Met358) (●) and AAT(Val358) (▲). B) Inhibition of porcine pancreatic elastase by AAT(Met358) (●) or AAT(Val358) (♦) in the presence of 10 mM N-chlorosuccinimide.

The AAT coding sequence is based on the normal human M1(Ala213) cDNA, but with modifications at resides 351 and/or 358, to render the AAT protein produced by AAV.vAAT resistant to oxidation. The mature AAT protein is a single chain of 394 amino acids and 3 carbohydrate side chains, with a total MW of 52 kDa[110,111]. AAT is a globular protein, with the carbohydrate side chains on the opposite end of the Met358 at the active site[112] (FIG. 2B). There are 9 α-helices and 3β-sheets. Like other serpins, the Met-Ser bond at the active site serves as pseudosubstrate for NE[40]. The interaction of AAT and NE is suicide for both. However, while AAT is a potent inhibitor of serine proteases, it can be rendered ineffective by oxidants. The major sources of oxidants in the lower respiratory tract are exogenous from inhaled oxidants (cigarette smoke, air pollutants) and endogenous from activated inflammatory cells[113]. Exposure of the normal M type AAT to oxidants results in oxidation of Met358 and Met351 at the active site to methionine sulfoxide, significantly reducing the ability of AAT to inhibit NE[1,32,39,114]. Consistent with these in vitro studies, the Crystal laboratory demonstrated that the AAT in lung epithelial lining fluid (ELF) of normal smokers had markedly reduced NE inhibiting capacity (FIG. 3), an observation confirmed by in vitro studies[33-38,41]. The oxidized AAT not only loses its anti-NE activity but also acts as a proinflammatory stimulus, activating monocytes and epithelial cells to generate chemoattractants[115,116]. Further evidence that oxidation of AAT occurs in vivo is the observation of elevated levels of oxidized AAT in serum in inflammatory disorders[117]. Replacement of Met358 with Val or Leu generates an AAT molecule that is effective at inhibiting neutrophil elastase, but is resistant to oxidation, functioning effectively in an oxidative milieu (FIG. 4). This has been confirmed by others[39,42,42,43,118], with the additional observation that the Met351 oxidation can also be prevented by substituting Val or Leu for Met351[39]. The "base" AAT allele from which the AAT expression cassette derived may be the common Z allele which was derived from the normal M1(Ala213) allele (FIG. 2C)[119], and which 95% of all AAT deficient individuals have.

Pharmaceutical Compositions

The invention provides a composition comprising, consisting essentially of, or consisting of the above-described gene transfer vector and a pharmaceutically acceptable (e.g., physiologically acceptable) carrier. When the composition consists essentially of the inventive gene transfer vector and a pharmaceutically acceptable carrier, additional components can be included that do not materially affect the composition (e.g., adjuvants, buffers, stabilizers, anti-inflammatory agents, solubilizers, preservatives, etc.). Men the composition consists of the inventive gene transfer vector and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the gene transfer vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, PA (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, w ater, immediately prior to use. Extemporaneous solutions and suspensions can be prepared from sterile powders, granules, and tablets of the kind previously described. In one embodiment, the carrier is a buffered saline solution. In one embodiment, the inventive gene transfer vector is administered in a composition formulated to protect the gene transfer vector from damage prior to administration. For example, the composition can be formulated to reduce loss of the gene transfer vector on devices used to prepare, store, or administer the gene transfer vector, such as glasses are, syringes, or needles. The composition can be formulated to decrease the light sensitivity and/or temperature sensitivity of the gene transfer vector. To this end, the composition may comprise a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the gene transfer vector, facilitate administration, and increase the efficiency of the inventive method. Formulations for gene transfer vector-containing compositions are further described in, for example, Wright et al., *Curr. Opin. Drug Discov. Devel.*, 6(2): 174-178 (2003) and Wright et al., *Molecular Therapy*, 12: 171-178 (2005))

The composition also can be formulated to enhance transduction efficiency. In addition, one of ordinary skill in the art will appreciate that the inventive gene transfer vector can be present in a composition with other therapeutic or biologically-active agents. For example, factors that control inflammation, such as ibuprofen or steroids, can be part of the composition to reduce swelling and inflammation associated with in vivo administration of the gene transfer vector. Immune system stimulators or adjuvants, e.g., interleukins, lipopolysaccharide, and double-stranded RNA, can be administered to enhance the AAT activity. Antibiotics, i.e., microbicides and fungicides, can be present to treat existing infection and/or reduce the risk of future infection, such as infection associated with gene transfer procedures, Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the inventive gene transfer vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the gene transfer vector in the composition administered to the mammal will depend on a number of factors, including the size (mass) of the mammal, the extent of any side-effects, the particular route of administration, and the like. In one embodiment, the inventive method comprises administering a "therapeutically effective amount" of the composition comprising the inventive gene transfer vector described herein. A "therapeutically effective amount" refers to an amount effective, at dosages and for periods of time necessary, to achieve a desired therapeutic result. The therapeutically effective amount may vary according to factors such as the extent of AAT deficiency, age, sex, and weight of the individual, and the ability of the gene transfer vector to elicit a desired response in the individual. The dose of gene transfer vector in the composition required to achieve a particular therapeutic effect typically is administered in units of vector genome copies per cell (gc/cell) or vector genome copies/per kilogram of body weight (gc/kg). One of ordinary skill in the art can readily determine an appropriate gene transfer vector dose range to treat a patient having a particular disease or disorder, based on these and other factors that are well known in the art. The therapeutically effective amount may be between $1 \times 10^{10}$ genome copies to $1 \times 10^{1}$ genome copies.

In one embodiment of the invention, the composition is administered once to the mammal. It is believed that a single administration of the composition will result in persistent expression of AAT in the mammal with minimal side effects. However, in certain cases, it may be appropriate to administer the composition multiple times during a therapeutic period to ensure sufficient exposure of cells to the composition. For example, the composition may be administered to the mammal two or more times (e.g., 2, 3, 4, 5, 6, 6, 8, 9, or 10 or more times) during a therapeutic period.

The present invention provides pharmaceutically acceptable compositions which comprise a therapeutically-effective amount of gene transfer vector comprising a nucleic acid sequence which encodes an oxidation-resistant AAT as described above.

Route of Administration.

In the normal humans, AAT is produced mainly by hepatocytes. However, AAT can be produced by many different cells/organs once the gene has been effectively transferred. The routes of administration that have been used for in vivo gene therapy for AAT deficiency include intravenous or intraportal vein (targeting liver hepatocytes), direct administration to skeletal muscle, intrabronchial (targeting the respiratory epithelium) and intrapleural.

All of these routes augment serum AAT levels. However, the challenge for effective AAT gene therapy is to achieve the threshold levels of AAT for successful protection of the alveolar structures from neutrophil proteolytic activity of serum AAT levels of at least about 11 μM in serum and 1.2 μM in alveolar ELF[7,8,11,13]. To achieve this "biochemical efficacy," both the serum and ELF protective levels of AAT must be demonstrated. Attempts of gene therapy targeted to the lung via delivery of AAV vector to the respiratory tract epithelium have been frustrated by the anti-pathogen immune and physical defenses of the epithelium, and the deficiency of viral receptors on the respiratory epithelial apical surface[122-125]. A variety of AAV vectors have been assessed by this route in experimental animals, including serotypes 1, 2, 5, 6, 9, 8, 9, rh.10, rh.20, rh.46, rh.64R1, hu.48R3, cy.5R4, and AAV6.2 (F129L)[24,25,30,125-127]. None have achieved therapeutic levels, and the respiratory epithelial route has not been developed for clinical trials. The skeletal muscle route has also been evaluated in experimental animals and in human trials using AAV1 and 2[28,128]. The clinical study with AAV2 to treat AAT deficiency, using doses of $2.1\times10^{12}$-$6.9\times10^{13}$ vector genomes (vg). observed low transient elevations of serum AAT[129]. A trial using AAV1 with doses up to $6\times10^{12}$ vg/kg had better success, with levels up to 5% of the target 11 µM[20,123,130,131]. In experimental animals, administration of AAV vectors by the intravenous route targets primarily the liver. Alternatively, portal vein delivery has been explored. The best results have been with AAV serotypes 8, 9 and 10 (see Chiuchiolo and Crystal[103] for review). Neither the intravenous nor intraportal routes has been tested in humans.

Figure 5A:
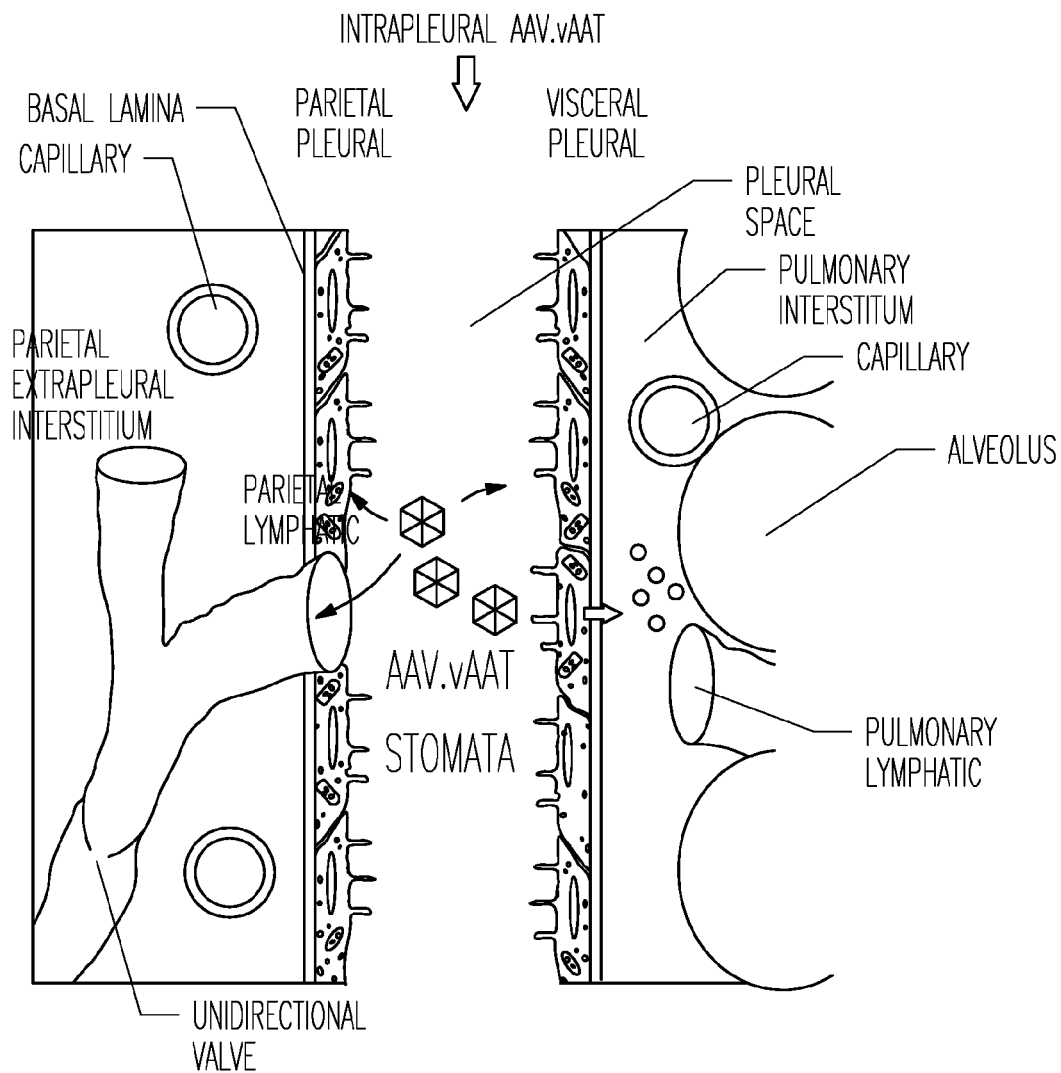
FIGS. 5A-C. Intrapleural administration of an AAV vector coding for AAT. A) Anatomy. B) Vector distribution following intrapleural administration, combining local lung delivery via vector transduction of the mesothelial cells lining the pleura, and systemic delivery via vector leaking to the systemic venous system and then primarily to liver hepatocytes. C) Delivery to the alveoli of AAT produced by AAV gene therapy to the pleura. The endothelial junctions are relatively loose, such that the levels of AAT (MW 52 kDa) in the interstitium are 60% of that in plasma. The epithelial junctions are tight, resulting in ELF AAT levels 5 to 10% of plasma. The locally (mesothelial cell) expressed RAT is delivered directly to the alveolar interstitium, while the liver (hepatocyte) expressed AAT diffuses from plasma to the interstitium. The AAT in the interstitium, and then to alveolar epithelial lining fluid (ELF).

AAT deficiency may also be addressed via pleural administration[132,133]. The pleura presents several structural features that make it an attractive site for gene delivery targeting both the lung parenchyma and systemic circulation, providing a large surface area for gene transfer that is easily accessible. The pleura is a thin serous membrane that encloses the chest cavity attaching to the chest wall (parietal pleura) and to the lung parenchyma (visceral pleura) merging at the chest hilum[134,135]. The parietal and visceral pleura contain a single layer of mesothelial cells surrounded by a thin layer of connective tissue rich in lymphatic and blood vessels connected to the systemic circulation (FIG. 5A). The pleura layers are separated by a pleural fluid (0.5 to 1 mL in humans)[135-140].

Figure 5B:
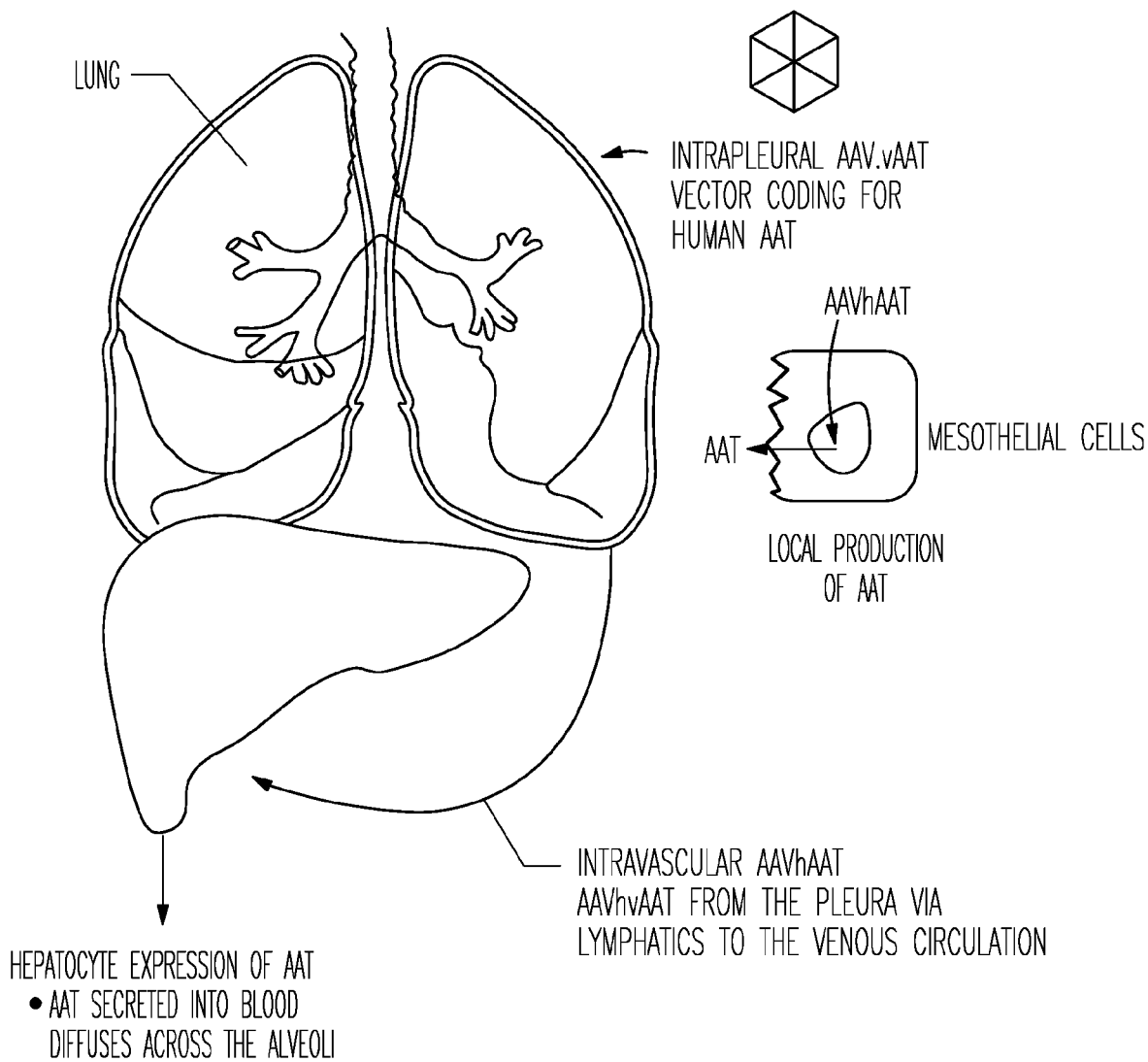
Figure 5C:
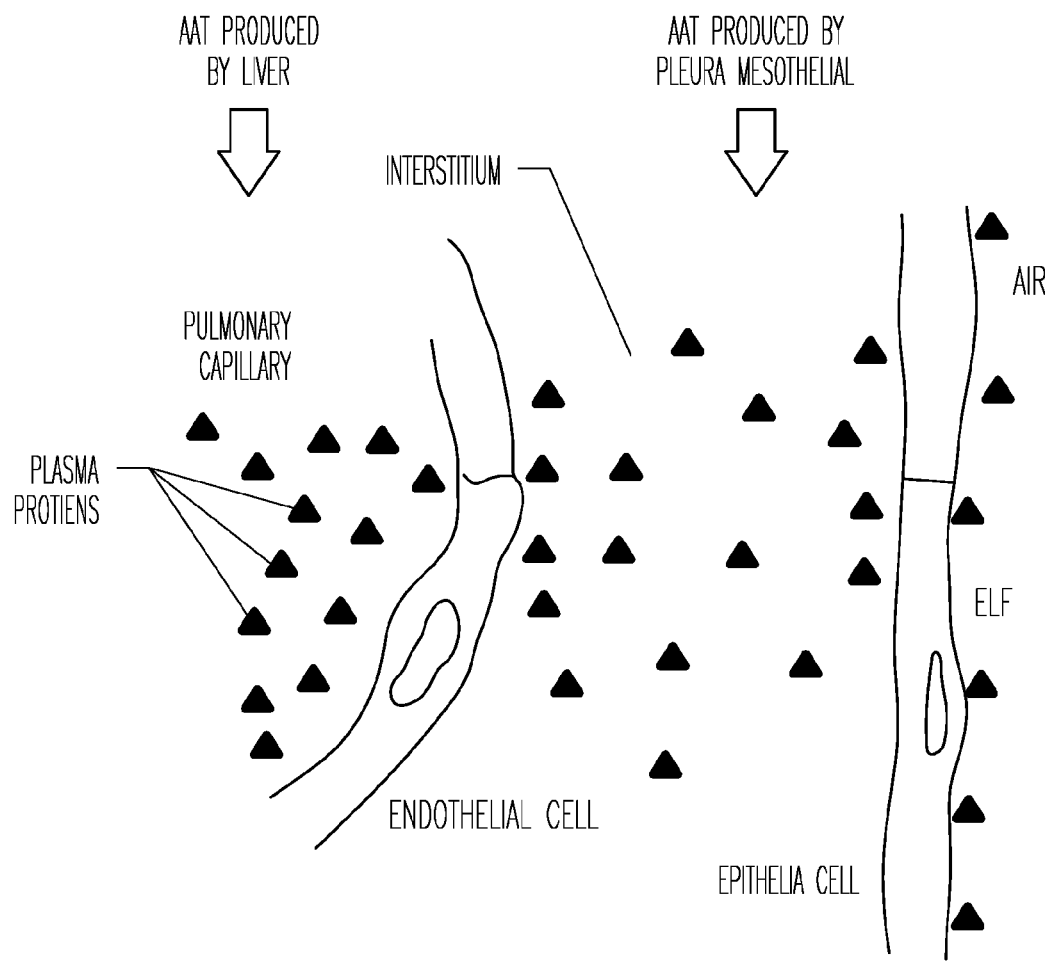

Compositions of the invention delivered to the pleura can genetically modify mesothelial cells lining the pleura and can also provide systemic delivery by vector leaking from the pleura via visceral pleural lymphatics to the systemic venous system and then primarily to liver hepatocytes (FIGS. 5B,C). The AAT produced by transduced pleural mesothelial cells are secreted and diffuse into the lung parenchyma. There may also be contribution from AAT carried by abundant lymphatic vessels from the visceral pleura that form an intercommunicating plexus that penetrate the lungs draining into the bronchial lymphatics[134,135,141]. The lymphatic system of the parietal pleura connects directly from the pleural space through stomata, a mechanism for parallel systemic distribution of the gene therapy vector to primarily the liver after intrapleural delivery[134,135,141]. Another advantage of targeting the pleura for gene therapy is the low risk of adverse effects of any inflammation induced by the gene therapy vector; in humans, inflammation in the pleura has no significant effect on lung function[142,143]. In regard to safety, intrapleural procedures (administration of saline or drugs, biopsies) are standard, 5-10 min procedures for pulmonary physicians, and extensive safety studies of intrapleural administration of a 1$^{st}$ generation AAV vector coding for AAT was carried out by the Crystal laboratory in mice and nonhuman primates, with no serious adverse events associated with the intrapleural[19].

Subjects

The subject may be any animal; including a human. human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

Preferred subjects include human subjects suffering from or at risk for the AAT deficiency. The subject is generally diagnosed with the condition of the subject invention by skilled artisans, such as a medical practitioner.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, childrens, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

The invention will be further described by the following non-limiting examples.

EXAMPLES

The animal experiments are designed to guarantee unbiased experimental design[148]. Experimental animals are randomly assigned to groups, and the investigators will be blinded when evaluating animal behavior. Males and females are used to address possible gender differences in AAV transduction, disease manifestation, or therapy response. The numbers of animals in each cohort have been chosen to yield statistically significant data.

Statistical Considerations.

The in vitro studies are performed in triplicate for 3 independent experiments. All data are presented as means±SEM unless otherwise stated. Animal studies are performed with n=5M, 5F mice/group to minimize animal usage while assessing gender difference and giving a reasonable chance that differences can be evaluated. Using a simple (two-sided) power calculation, a two-fold difference can be seen with an alpha of 0.05 and a power of 0.9 if the variance in the measured parameter was 50%, Statistical analysis of clinical pathology is performed using the SAS Software System version 9.2. A t-test will be used for comparison of two groups and ANOVA for more groups to assess treatment-related effects with gender at each time point. Where there was a significant trend across groups ($p<0.05$) by ANOVA, Tukey's multiple comparison tests is used to assess pairwise differences among all groups, where n=10M and 10F per group.

AAT Levels.

ELISA, using a highly purified AAT standard[151]. For serum, the AAT levels are expressed as µM. Lung ELF is obtained by fiberoptic bronchoscopy and lavage. The recovered fluid is a mixture of the saline used to recover the ELF and the actual ELF. The volume of recovered ELF is quantified using the urea method[165]. and the level of AAT expressed in µM using ELF volume as the denominator[14].

AAT Function.

Figure 6A:
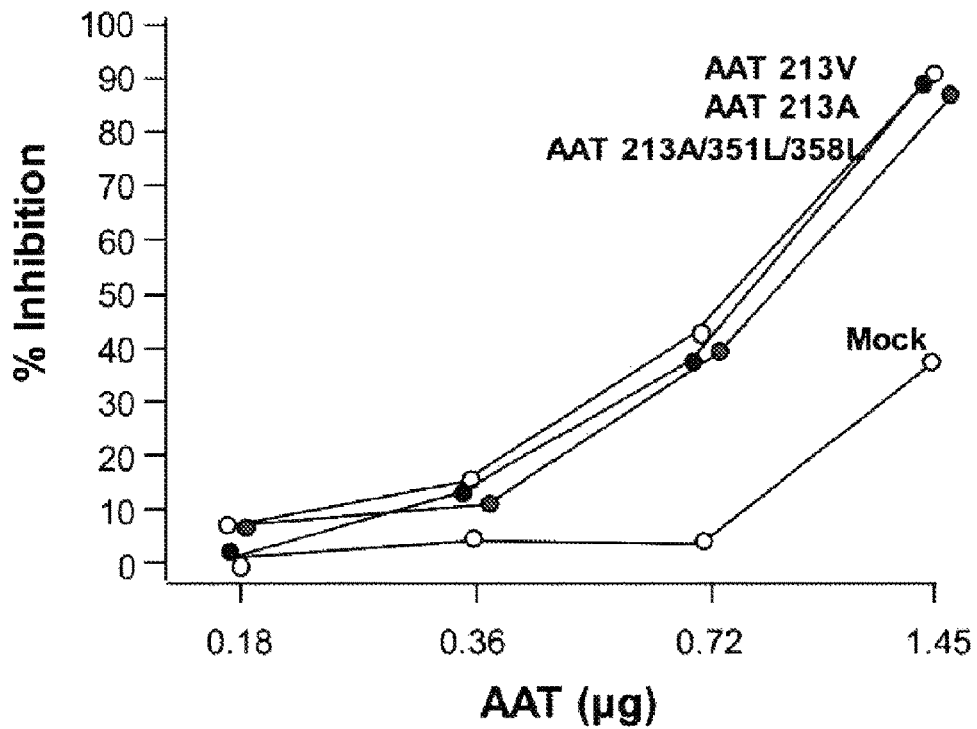
FIGS. 6A-B. In vitro assessment of neutrophil elastase inhibition by AAT variant expression cassettes. HEK293T cells were transfected with plasmids pAAV-AAT(V213), pAAV-AAT(A213), pAAV-AAT(A213)-M351L, M358L or mock transfected. Dilutions of AAT protein collected from the supernatant were quantified and pre-incubated with or without the oxidizer N-chlorosuccinimide (NCS). AAT was then incubated with neutrophil elastase. Neutrophil elastase inhibition was measured by the addition of N-Suc-Ala-Ala-Ala-p-nitroanilide substrate and measuring p-nitroanilide product formation by spectrophotometric measurement at 410 nm. A) Neutrophil elastase inhibition curve. B) Neutrophil elastase inhibition in the presence of oxidizing NCS.
Figure 6B:
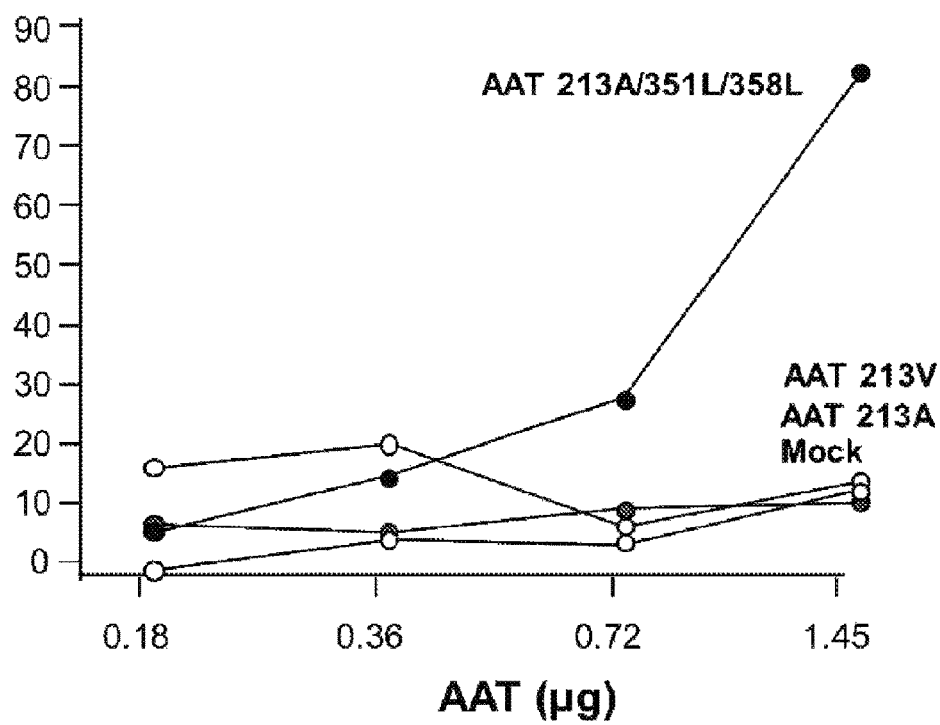

Anti-NE capacity±oxidants is assessed using the assays described in FIG. 6. The activity in serum and ELF is expressed in µM[14]. Isoelectric focusing. To quantify the relative amounts of the Z AAT and AAV.vAATAAT in serum and ELF, using standard methods[2,22]. AAV.vAAT-related immunity assays. The capsid of AAV.vAAT is "foreign" to the patient, and based on prior gene therapy studies[19,166], there will be humoral and perhaps cellular immunity induced to some degree against the AAV8 capsid, and although far less likely, to the AAT protein expressed by AAV.vAAT. These assays include serum anti-AAV8 antibodies (neutralizing antibody titer using AAV8 reporter transgene expression in 2V6.11 cells[167]), blood mononuclear cells anti-AAV8 cellular immunity (ELISPOT), serum anti-AAT antibodies and blood mononuclear cells anti-AAT cellular immunity (ELISPOT).

Using the Normal M1(A213) AAT Coding Sequence as a Base, Assess Combinations of Met, Leu, and Val at Positions 351 and 358.

Objectives.

All of the current gene therapy strategies for AAT deficiency deliver the normal human M1 (Val213) cDNA using an AAV gene transfer vector[2,19-31,126]. The expression cassette of AAV.vAAT is based on M1(Ala213) which 95% of the recipients of AAV.vAAT express and which was derived from the normal M1(Ala213) allele (FIG. 20). M1(A 1213) oxidant-resistant forms of AAT are assessed in vitro to determine useful variants for use in AAV.vAAT (Table I). Numerous studies have demonstrated that the methionine at positions 351 and 358 can be oxidized leaving AAT inactive[1,32-35,39,41,149,150] Changing these residues to valine or leucine have been shown to prevent oxidation while maintaining the ability to inhibit NE[39,43,118] (FIG. 4). The preliminary data shows that the AAT variant candidate plasmid with a Leu change at positions 351/358 was more resistant to the oxidizing agent N-chlorosuccinimide (NCS) compared with the M1(A213) or M1(V213) AAT (FIG. 6). The basic assay is to transfect the expression cassette plasmids described in FIG. 6 into 293T cells in anti-protease free cell culture media, and test the resulting media for anti-neutrophil elastase inhibition activity±oxidants.

TABLE 1

Alternative oxidation-resistant variants of AAT Residue

| 351 | 358 |
|---|---|
| M | M |
| V | M |
| M | V |
| V | V |
| L | M |
| M | L |
| L | L |
| L | V |
| V | L |

[1]Single letter amino acid code variants at residues 351 and 358.

Detailed Methods.

Site-directed mutagenesis is used to change the methionine residues at amino acid positions 351 and 358 to valine or leucine in the M1(A213) allele cDNA in all possible combinations of single and double variants (Table I). Plasmids encoding for the AAT oxidant variants or the parental AAT will be transfected into 293T cells in serum-free media and the secreted AAT proteins collected in the supernatant after 72 hr. The amount of AAT protein in the supernatant is quantified by ELISA using a highly purified, validated standard[151]. Two approaches are used to determine the oxidation resistance of AAT candidates. First, the parental AAT and the AAT variants are pre-incubated with increasing concentrations of oxidizing agents such as NCS, $H_2O_2$, or cigarette smoke extract before incubation with NE Inhibition of NE is measured by addition of the substrate N-Suc-Ala-Ala-Ala-p-nitroanilide[152]. The product of NE hydrolysis, p-nitroanilide, is assessed by spectrophotometric measurement at 410 nm. Second, the AAT constructs are pre-incubated with a fixed amount of oxidizing agent for varying amounts of time and then evaluated for their ability to inhibit NE The association rate ($K_{assoc}$) is calculated for each of the oxidized AAT variants and parental AAT by determining the inhibition activity as a function of time[32,98,153,154]. The AAT variants are scored (>85% inhibition—5 points; 70-85%—4; 55-70%—3; 40-55%—2; 25-40%—1; <25%—0) based on their ability to inhibit neutrophil elastase after exposure to oxidizing agents at different concentrations and times. Studies may also be carried out to evaluate variants for inhibition of cathepsin G, another serine protease that is inhibited by AAT and has been show n to play a role in the development of pulmonary emphysema[155].

Intrapleural Administration of AAV.vAAT to Experimental Animals Results in Persistent, High Levels of Oxidation-Resistant Human RAT in Serum and Lung Epithelial Lining Fluid.

Figure 7A:
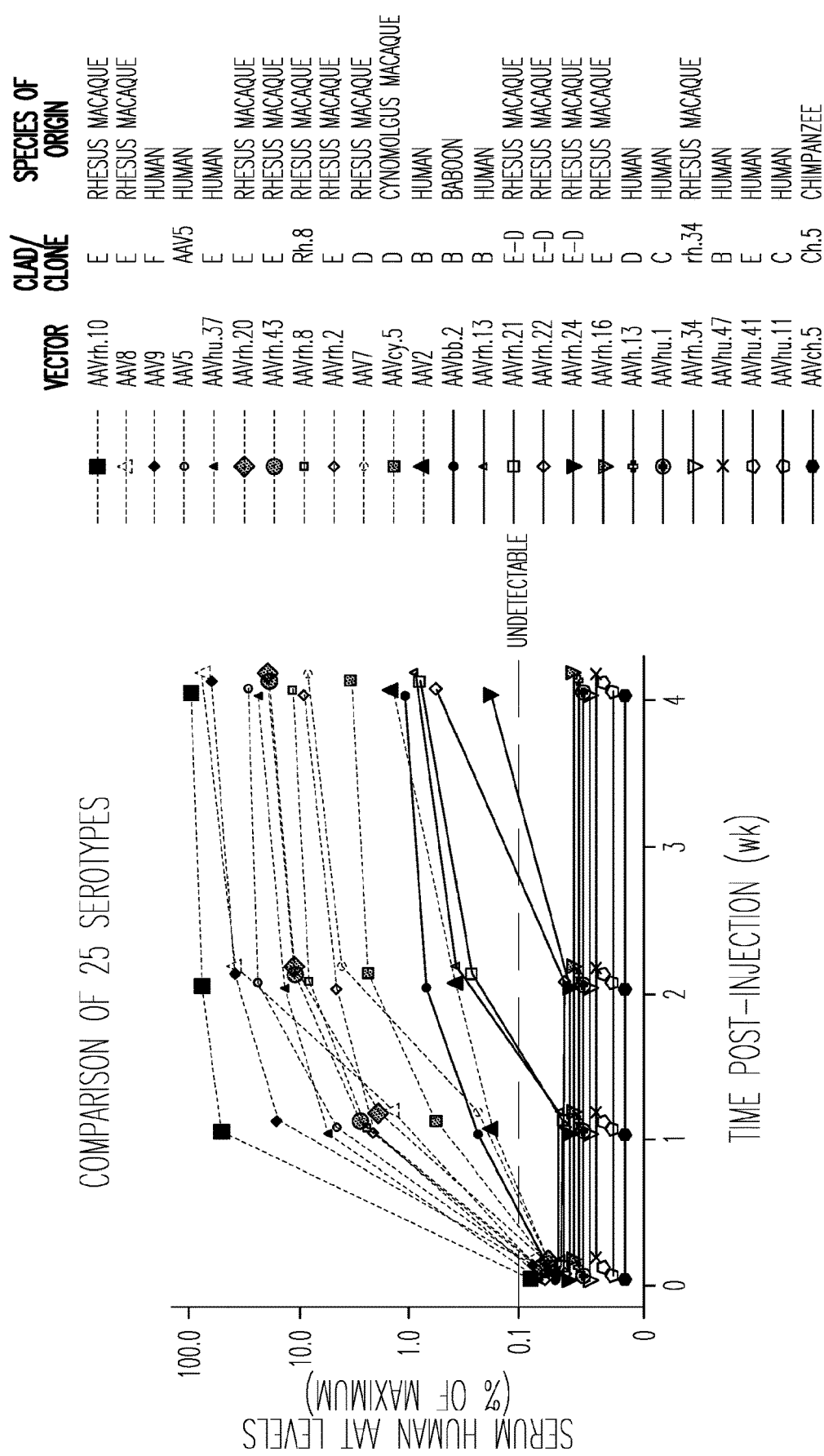
FIGS. 7A-C. Intrapleural administration of AAV vector coding for human AAT. A) Comparison of 25 different AAV serotypes for AAT expression efficiency after intrapleural administration. The AAV vectors, pseudotyped as indicated and containing the AAT expression cassette and the AAV2 inverted terminal repeats, were administered intrapleurally ($5 \times 10^{10}$ genome copies, gc) to male C57BL/6 mice (n=5/group). Serum AAT levels were measured by ELISA up to 4 wk after administration. The data shown are percentages of means of 5 mice, with the levels at 4 wk of AAVrh.10 (in red) and AAV8 yielding the highest levels. The dashed line represents the assay limit of detection. B) Persistent AAT levels in serum after AAVrh.10RAT intrapleural administration. AAVrh.10AAT ($10^{11}$ gc) was administered intrapleurally to male 0573116 mice (n=4/group) and serum human AAT levels were assayed by ELISA up to 24 wk following administration. Values shown are means±standard error. C) Human AAT levels in bronchoalveolar lavage fluid compared to serum at 8 wk after intrapleural administration of $10^{11}$ gc AAVrh.10hAAT(C57BL/6 mice, n=4). Human AAT levels are referenced to total protein (mean±standard error).
Figure 7B:
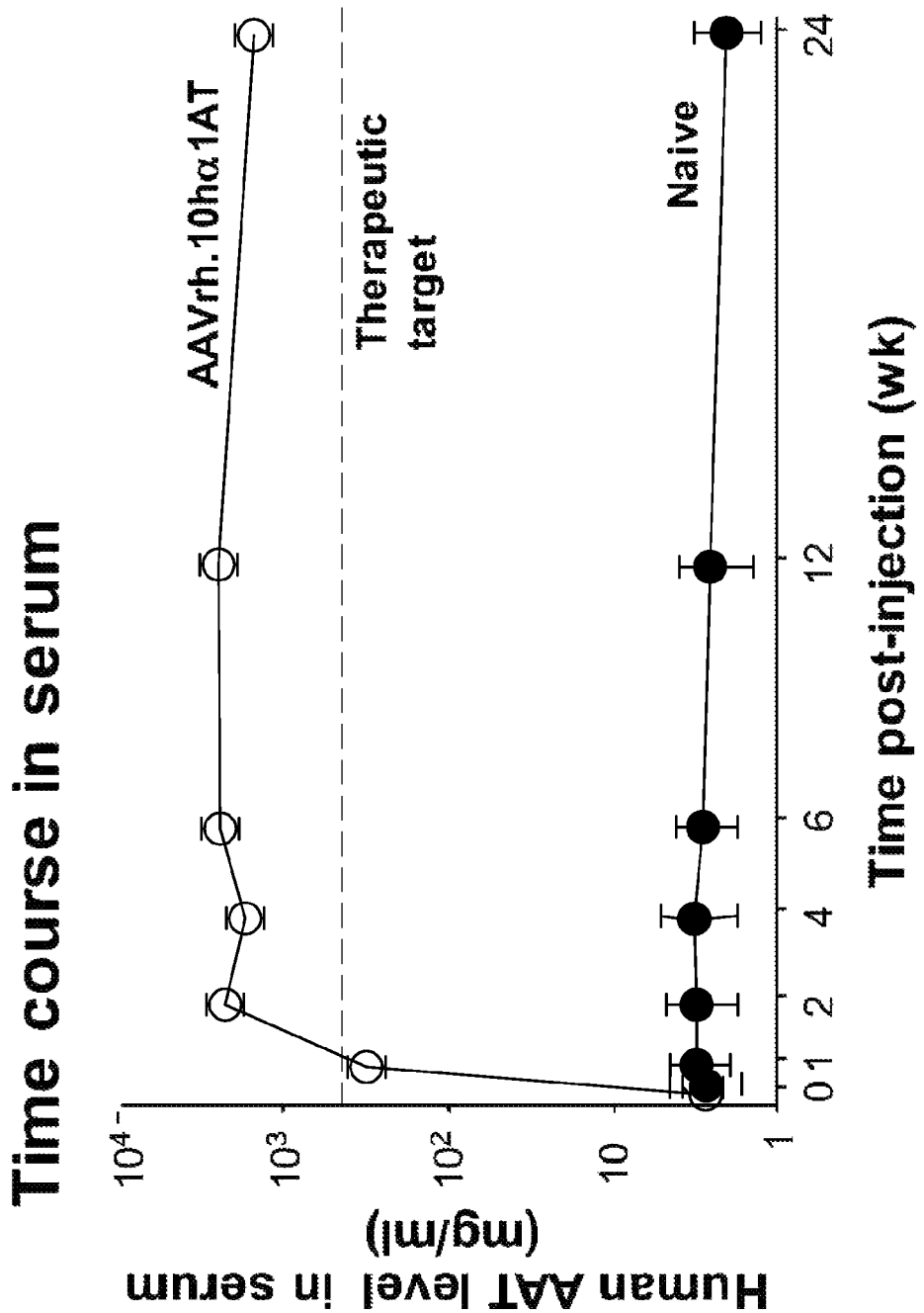
Figure 7C:
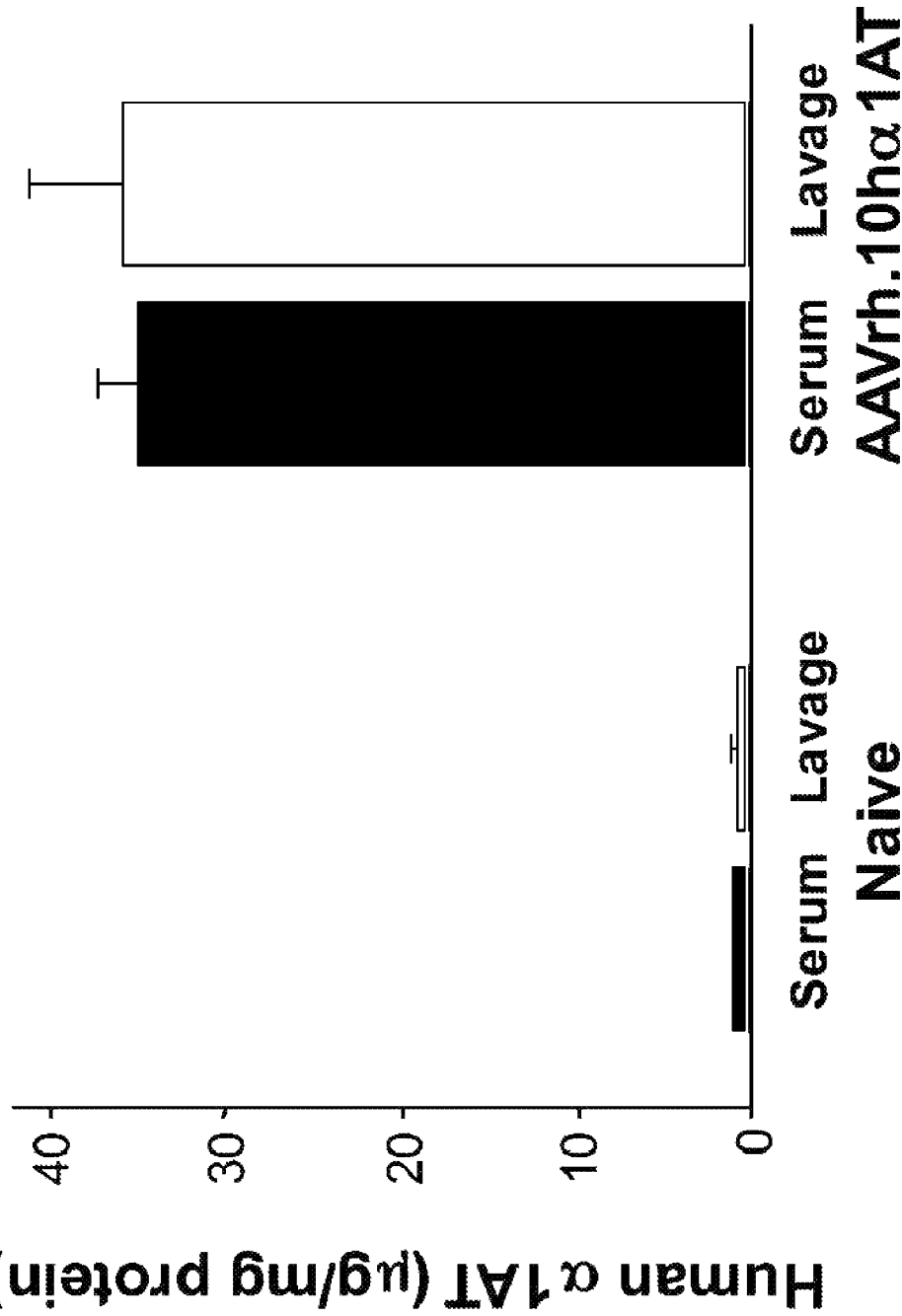
Figure 8:
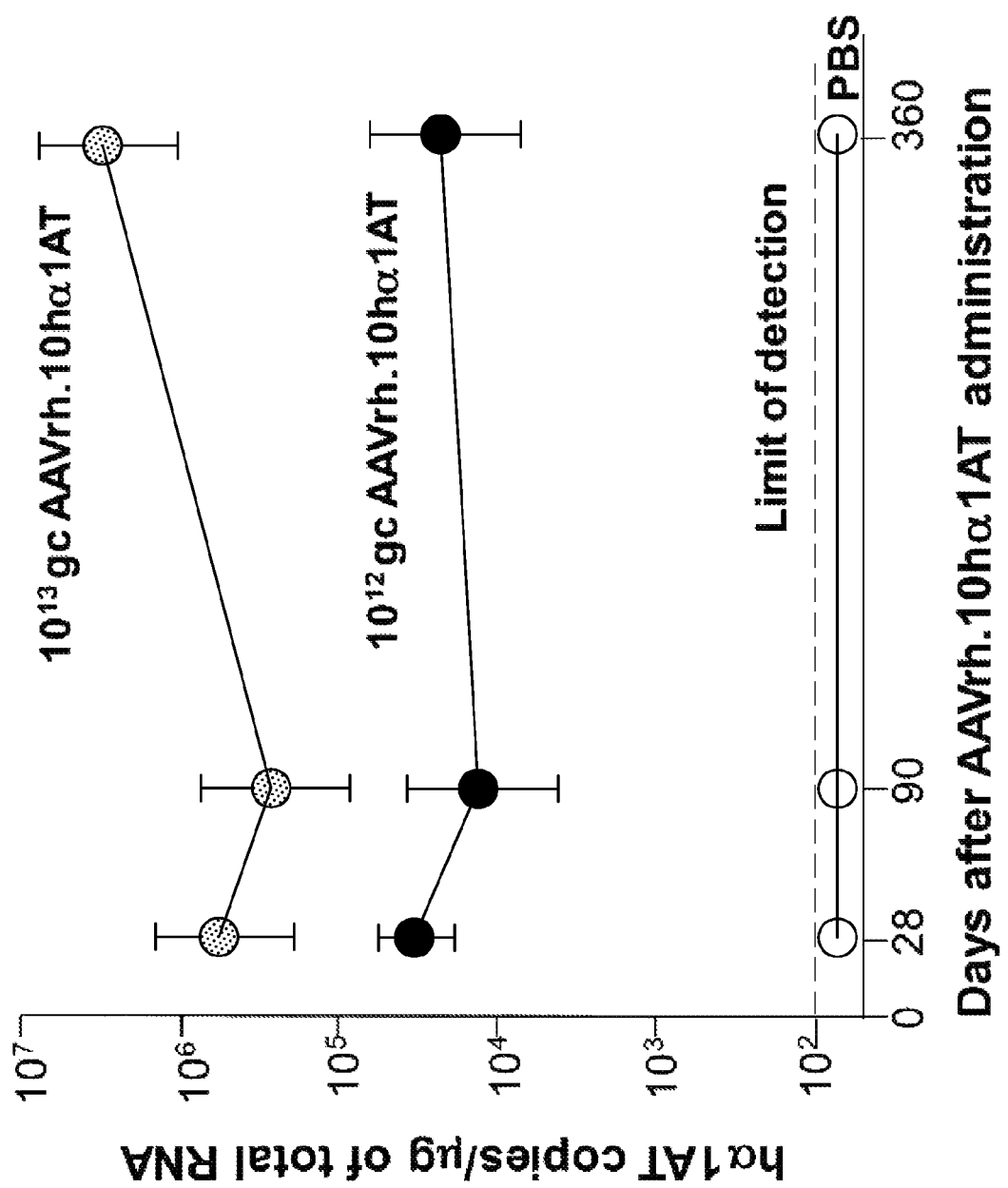
FIG. 8. Human AATmRNA expression in the pleura of nonhuman primates 1 yr following a single intrapleural AAVrh.10hAAT vector administration. Human AAT mRNA expression was assayed in tissue sections by TaqMan quantitative FCR at 28, 90 and 360 days after single intrapleural administration of PBS or AAVrh.10hAAT ($10^{12}$ or $10^{13}$ gc, n=4 per dose). mRNA copies were normalized/µg total RNA. Data presented as the geometric mean±SE.

In a mouse preclinical model, De et al[2] demonstrated that an AAV5-based vector expressing human AAT produced high, sustained levels of the protein (1 mg/ml) in serum via the intrapleural route compared to intramuscular administration at the same dose. The therapy approach resulted in levels of AAT in the lung similar to that in serum[2]. In a comparison of 25 different AAV serotypes in mice, De et al[22] demonstrated that 2 Glade E AAV nonhuman primate vectors, AAVrh.10 and AAV8 were the most effective, with intrapleural administration providing high, long term delivery of human normal M type AAT; AAV8 is a bit slower than AAVrh.10, but both made the same level of expression by 4 wk, 2.5-fold above the therapeutic threshold of 11 μM. The Crystal laboratory chose AAVrh.10 for follow up studies. High serum levels with AAVrh.10 were sustained through 24 wk, the latest point of the study (FIG. 7B). Importantly, similar levels were achieved in serum lung ELF, demonstrating "biochemical efficacy" (FIG. 7C). AAVrh.10 delivered by the intrapleural route was show n to be safe in a safety and toxicology study with 280 mice and 36 nonhuman primates[19]. The intrapleural vector transfer resulted in high levels of human AAT mRNA localized to the lung pleura mesothelioma that persisted for at least 6 months in mice[19] and for at least 1 yr after a single vector administration in nonhuman primates[19], the length of the study (FIG. 8). In the context that AAT expression following intrapleural AAV8 and AAVrh.10 are similar AAV.vAAT could also be based on AAV serotypes rh.10 or 8.

AAV.vAAT may comprise the CAG promoter driving an oxidation-resistance, NE inhibiting human AAT coding sequence based on AAT(Ala213) packaged in the AAV8 capsid (FIG. 2A). Studies are carried out in mice to demonstrate that the intrapleural route of administration of AAV.vAAT provides sufficient levels of anti-NE, oxidation-resistant human AAT in serum and lung epithelial lining fluid (ELF). Studies of the Crystal laboratory with AAV8 and its similar Glade E capsid AAVrh.10 (FIG. 7), have shown that intrapleural route is feasible. Identical doses of AAV.vAAT variants are administered by the intravenous route, the route that delivers AAV vectors, including AAV8, primarily to the liver, the conventional route AAV vectors are administered for systemic metabolic diseases[157-159]. The studies are carried out as a function of dose in half-log increments ($4\times10^{19}$, $1\times10^{11}$ and $4\times10^{11}$ gc; the 4×10" gc dose scales to ~$4\times10^{14}$ gc in humans, the highest dose that can be used safely in adult humans without concomitant liver toxicity[160]). Over a 6 month period, serum and lung ELF (recovered by lavage) are assessed for human AAT levels and anti-NE capacity±oxidant stress. Based on the data from the Crystal laboratory and the literature[103], if AAV vectors provide stable expression for 6 months, the levels can persist for the lifetime of the experimental animal[19,161].

Administration by the intrapleural route provides persistent, high level expression of oxidant-resistant, NE functioning human AAT in serum and lung ELF.

The cDNA from oxidant resistant α1AT constructs are packaged into AAV8 (FIG. 2A). AAV.vAAT is produced using adherent 293T cells (see below for a detailed description of AAV.VvAAT manufacturing).

In Viva Assessment.

AAV.vAAT is administered at 3 doses ($4 \times 10^{10}$, $10^{11}$, $4 \times 10^{11}$) by the intrapleural and intravenous routes to C57Bl/8 mice (C57Bl/6 are used because they do not recognize human AAT as "foreign")[22], with controls AAV8hAAT (the identical vector as AAV.vAAT but with the normal AAT(Ala213) cDNA) and AAV8Null (the identical vector as AAV.vAAT but with no AAT in the expression cassette). Only the highest dose $4 \times 10^{11}$ gc is used for the controls. Serum and lung ELF is assessed at 0 (pre-therapy), 14, 28, 90 and 180 days for human AAT levels and anti-NE capacity in the absence or presence of NCS (Table 2).

TABLE 2

In Vivo Assessment of AAV.vAAT[1]

| Vector[2] | Route[3] | Dose (genome copies) |
|---|---|---|
| AAV.vAAT | IP | $4 \times 10^{10}$, $10^{11}$, $4 \times 10^{11}$ |
| | IV | $4 \times 10^{10}$, $10^{11}$, $4 \times 10^{11}$ |
| AAV8hAAT control | IP | $4 \times 10^{11}$ |
| | IV | $4 \times 10^{11}$ |
| AAV8Null control | IP | $4 \times 10^{11}$ |
| | IV | $4 \times 10^{11}$ |

[1]All studies with C57Bl/6 mice, n = 5M, 5F at each dose vector, dose and time point (0, 28, 90, 180 days), total n = 400 mice; AAT assays include: human AAT levels (ELISA) and anti-NE capacity in the absence or presence of NCS (see Johnson & Travis[1] for details);
[2]Vectors as defined in the text;
[3]IP = intrapleural, right side, 100 μl (see De et al[2] for details); IV = intravenous, tail vein, 100 μl (see Pagovich et al[3] for details). All available data supports the concept that the IP route is superior to the IV route for clade E AAV vectors[2], the IV route is included in these studies to insure this holds for AAV.vAAT.

Detailed Methods for a Formal Toxicology Study.

Based on Crystal laboratory recent experience with the FDA and the Crystal laboratory experience with a GMP 1st generation AAVrh, 10 vector (same Glade as AAV8) toxicology study[107], and the FDA website guidance that neither the use of multiple species nor nonhuman primates is a default[163], we expect that the only required toxicology study will be in nice. The total amount of GMP vector required is $5 \times 10^{15}$ gc. The study will evaluate two doses ($10^{11}$ and $10^{12}$ genome copies; $10^{12}$ gc is ½ log greater than the likely highest dose scaled to humans) administered by either the intrapleural or intravenous route to C57BL/6 mice to assess; (1) safety following vector administration; (2) biodistribution of the vector; and (3) hα1AT mRNA expression in chest cavity organs (Table 3). General safety, hematology, serum chemistry, histopathology parameters, vector genome distribution and transgene expression will be evaluated at 4 time points (4, 28, 90, 180 days) after a single AAV.vAAT administration.

Table 3 describes a toxicology study. The design is similar to that carried out for IND BB IND 16008 for a 1st generation AAV vector for AAT deficiency (AAVrh.10hAAT), this toxicology study has been published[19,162].

TABLE 3

Mouse Safety and Toxicology Study Design

| Treatment/ route [1] | Number of animals per time point | Complete blood count | Serum chemistry | Genome distribution | AAV8 neutralizing antibodies | Histopathology | hAAT mRNA |
|---|---|---|---|---|---|---|---|
| PBS (IP) | 10F/10M | ■ | ■ | ■ | ■ | ■ | ■ |
| AAV.vAAT ($10^{11}$ gc, IP)[2] | 10F/10M | ■ | ■ | ■ | ■ | ■ | ■ |
| AAV.vAAT ($10^{12}$ gc, IP) | 10F/10M | ■ | ■ | ■ | ■ | ■ | ■ |

[1] Administered on day 0 by the interpleural (IP) or intravenous (IV) route, doses $10^{11}$ or $10^{12}$ gc; the IV group at the highest dose ($10^{12}$ gc) is used as a worst case scenario of inadvertent IV administration, gc—genome copies.
[2]10 M/10 F at each dose group will be assessed at day 0 (pretherapy) 4, 28, 90 and 180 days for the parameters listed; animals will be assessed twice daiy for morbidity/mortality; body weight assessed pre-dosing and weekly. The list of all parameters and methods will be identical to the GMP toxicology study for the 1st generation AAVrh.10hAAT vector carried out by Chiuchiolo et al[19]

Manufacturing

Many CROs have experience in producing GMP vectors for in viva gene therapy clinical studies and in designing and carrying out formal toxicology studies, including Weill Cornell Belfer Gene Therapy Core Facility (BGTCF; a core facility run by the Crystal laboratory that carries out fee-for-service contract production of GMP gene therapy vectors for academia and industry) as they have experience in producing AAV8 for a clinical trial; and in producing GMP vectors expressing human AAT.

Figure 9:
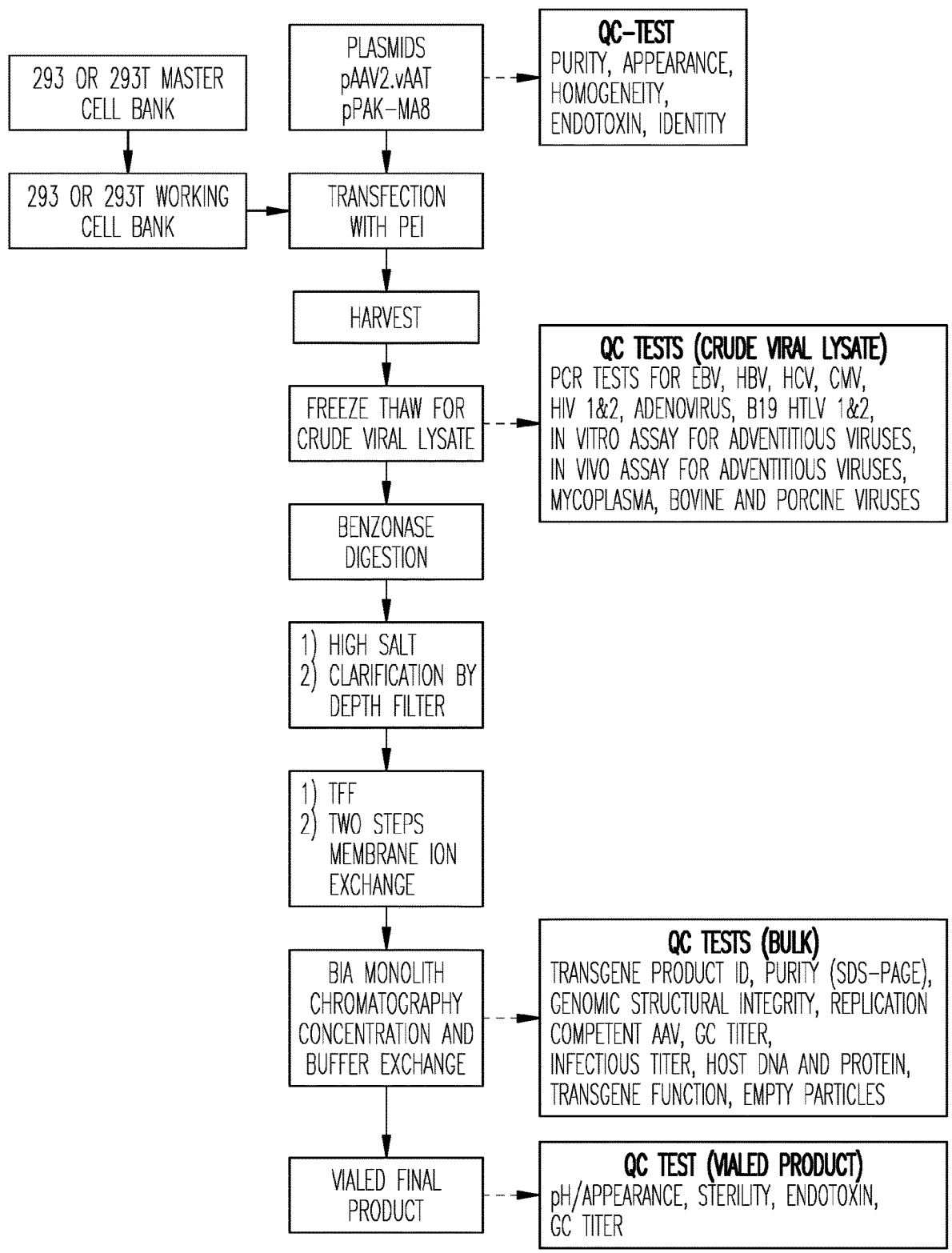
FIG. 9. AAV GMP production scheme. The center path indicates the steps in the manufacture of AAV.vAAT. Boxes to the left indicate the source of the production cells and boxes to the right of each step are the quality control assays.
Figure 10:
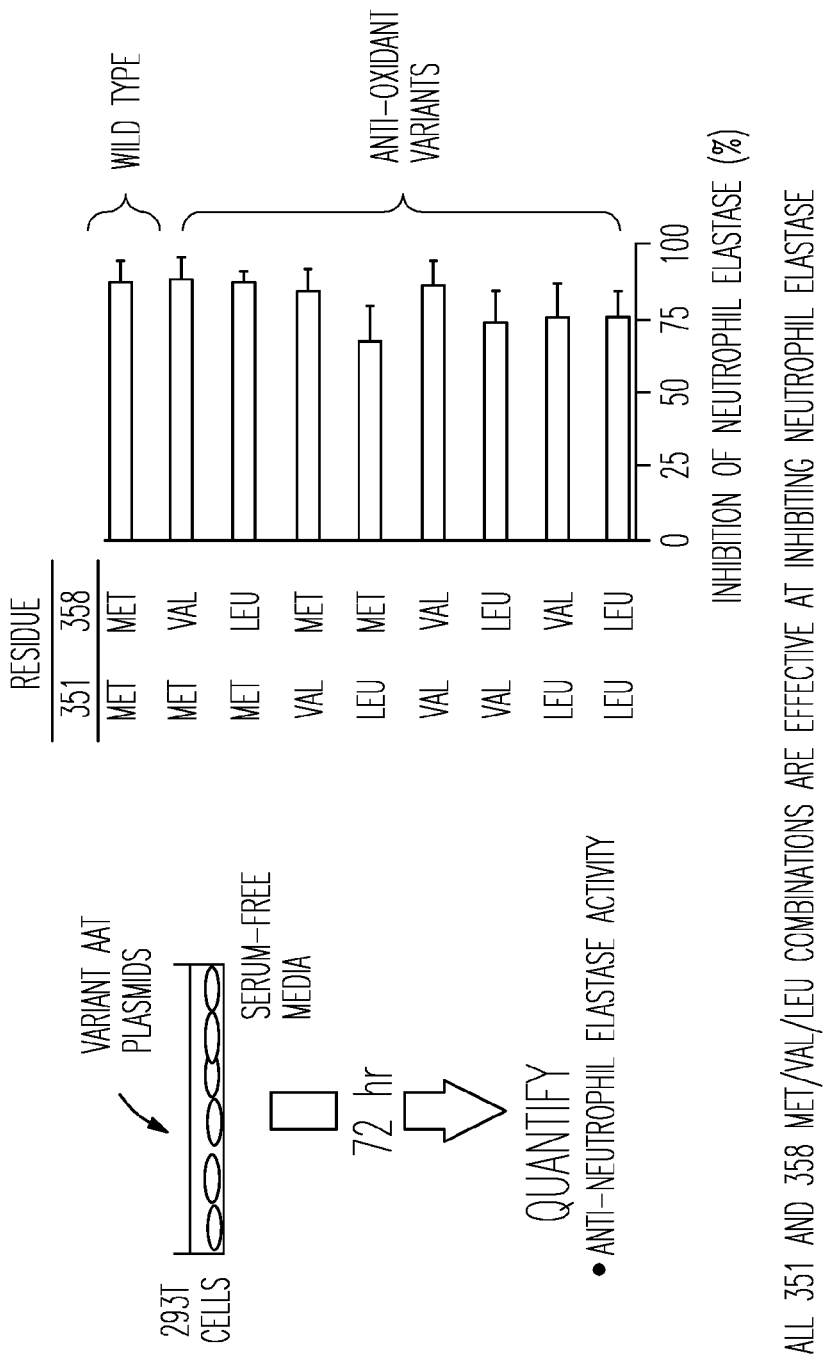
FIG. 10. in vitro comparison of oxidation-sensitive and oxidation-resistant variants of human AAT to inhibit neutrophil elastase. All 351 and 358 Met/Val/L variant combinations were effective at inhibiting neutrophil elastase.
Figure 11:
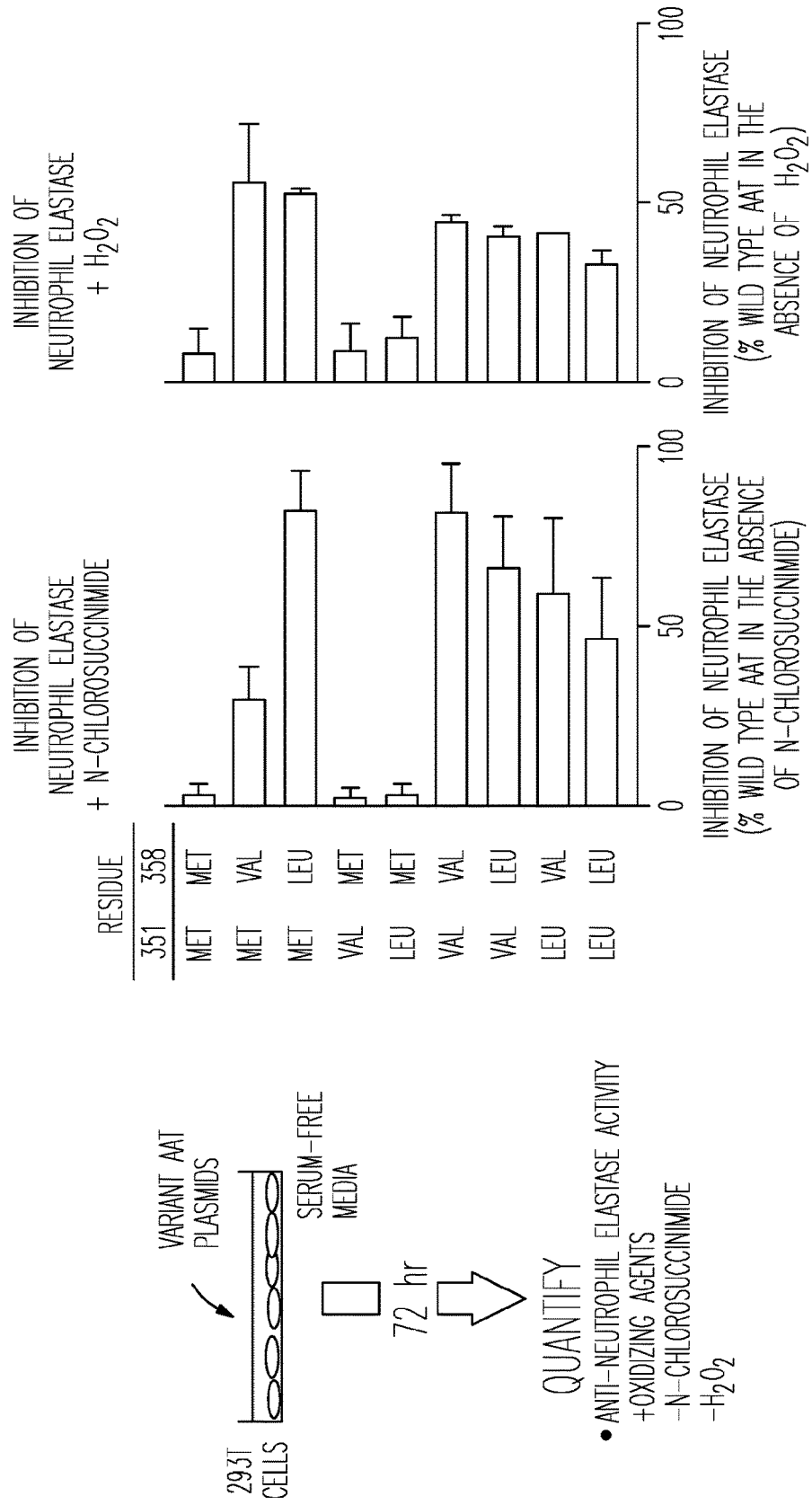
FIG. 11, In vitro comparison of oxidation-sensitive and oxidation-resistant variants of human AAT to inhibit neutrophil elastase in the presence of an oxidant stress. Replacement of Met358 enhances efficacy.
Figure 12:
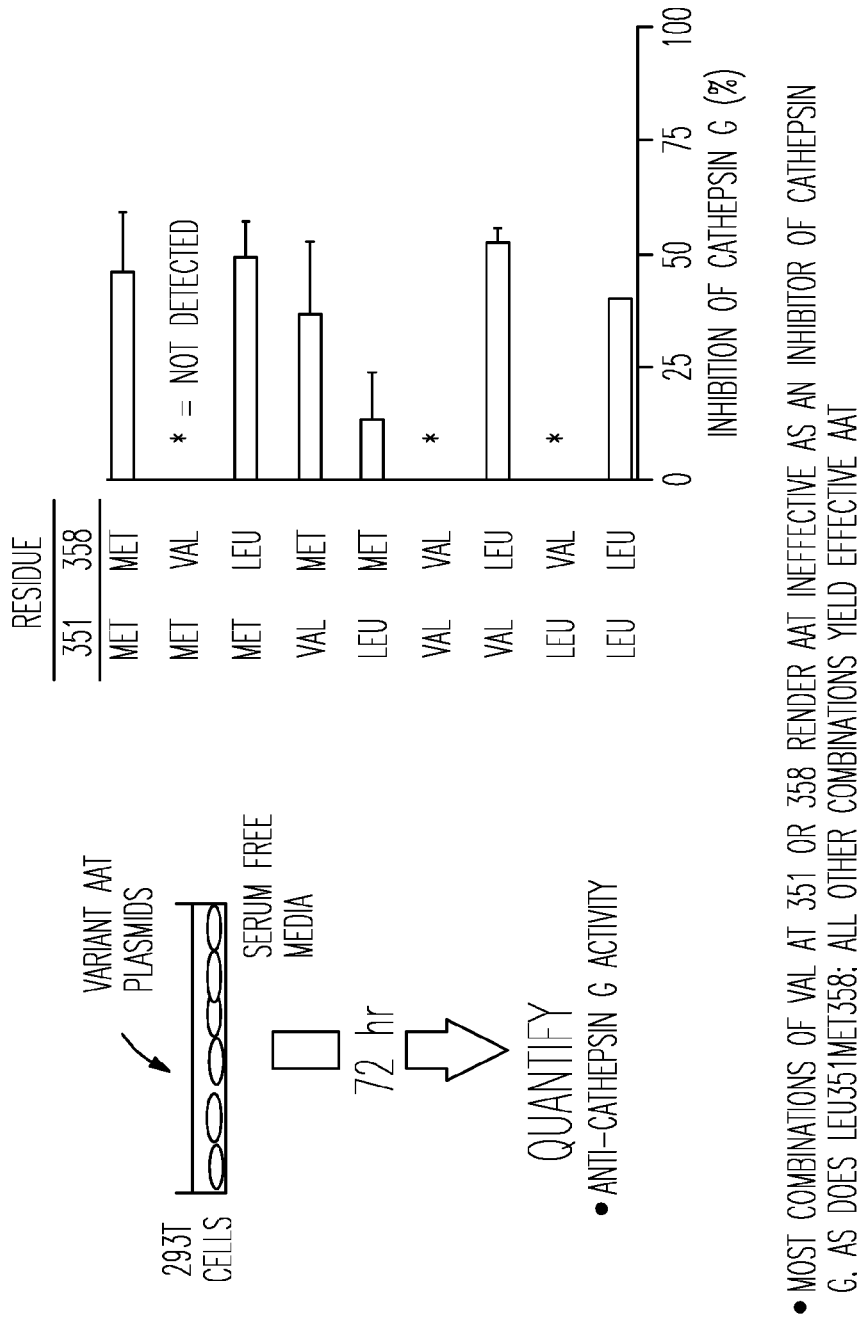
FIG. 12. In vitro comparison of oxidation-sensitive and oxidation-resistant variants of human AAT to inhibit cathepsin G. Some single substitutions and double substitutions yield effective AAT.
Figure 13:
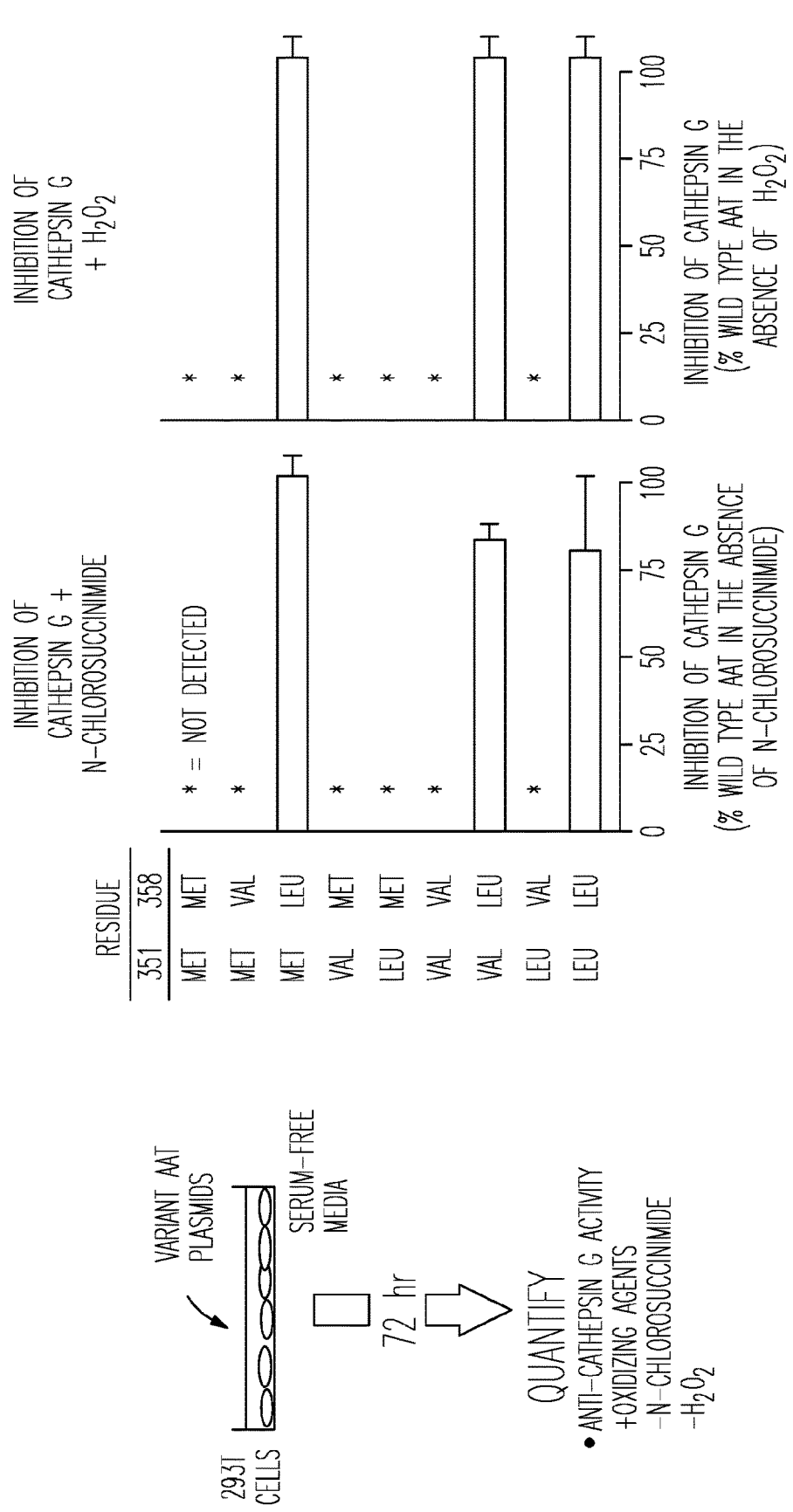
FIG. 13. In vitro comparison of oxidation-sensitive and oxidation-resistant variants of human AAT to inhibit cathepsin G in the presence of an oxidant stress. One single substitutions and two double substitutions yield effective AAT.
Figure 14:
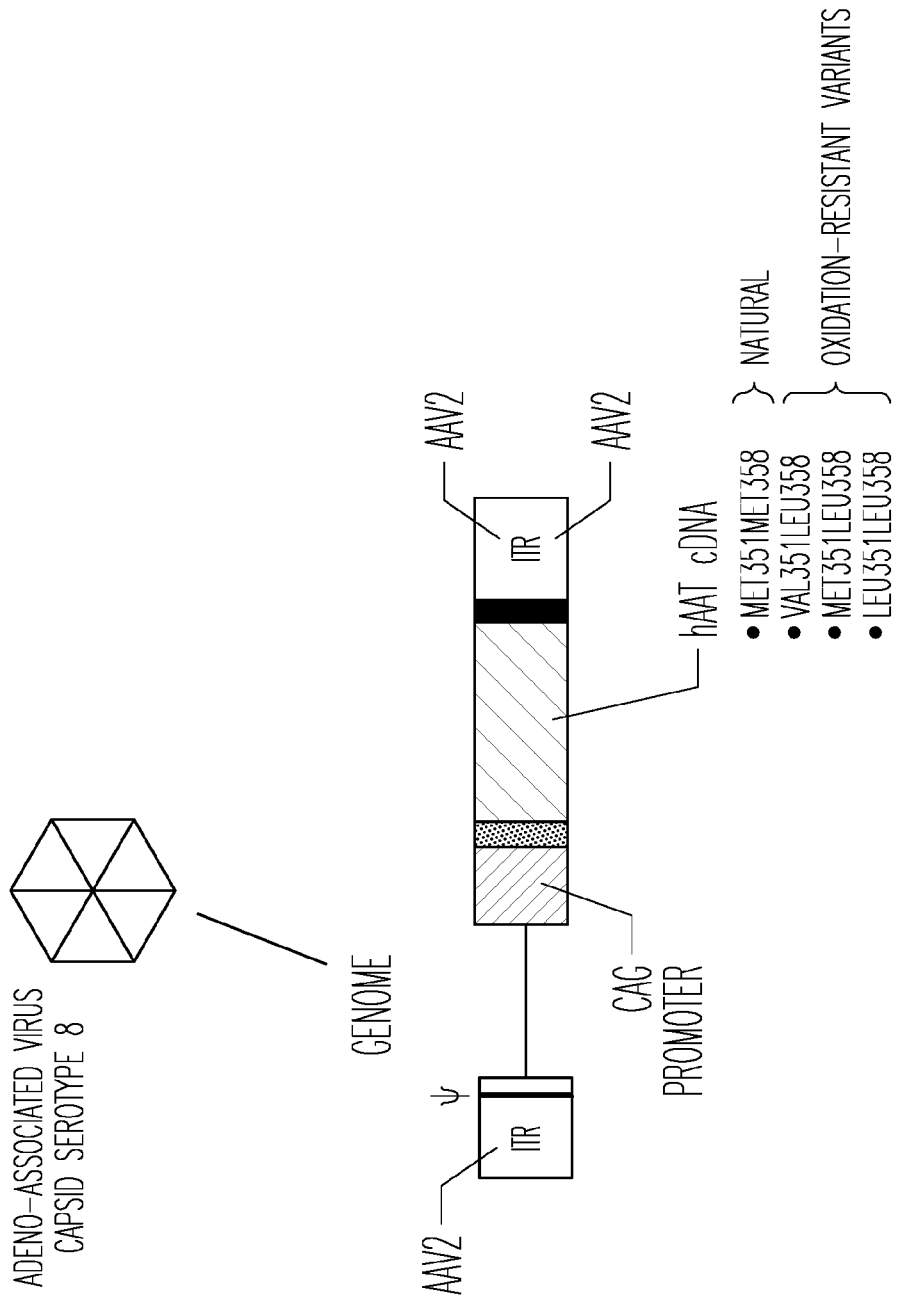
FIG. 14. Schematic of vectors for in vivo experiments.
Figure 16:
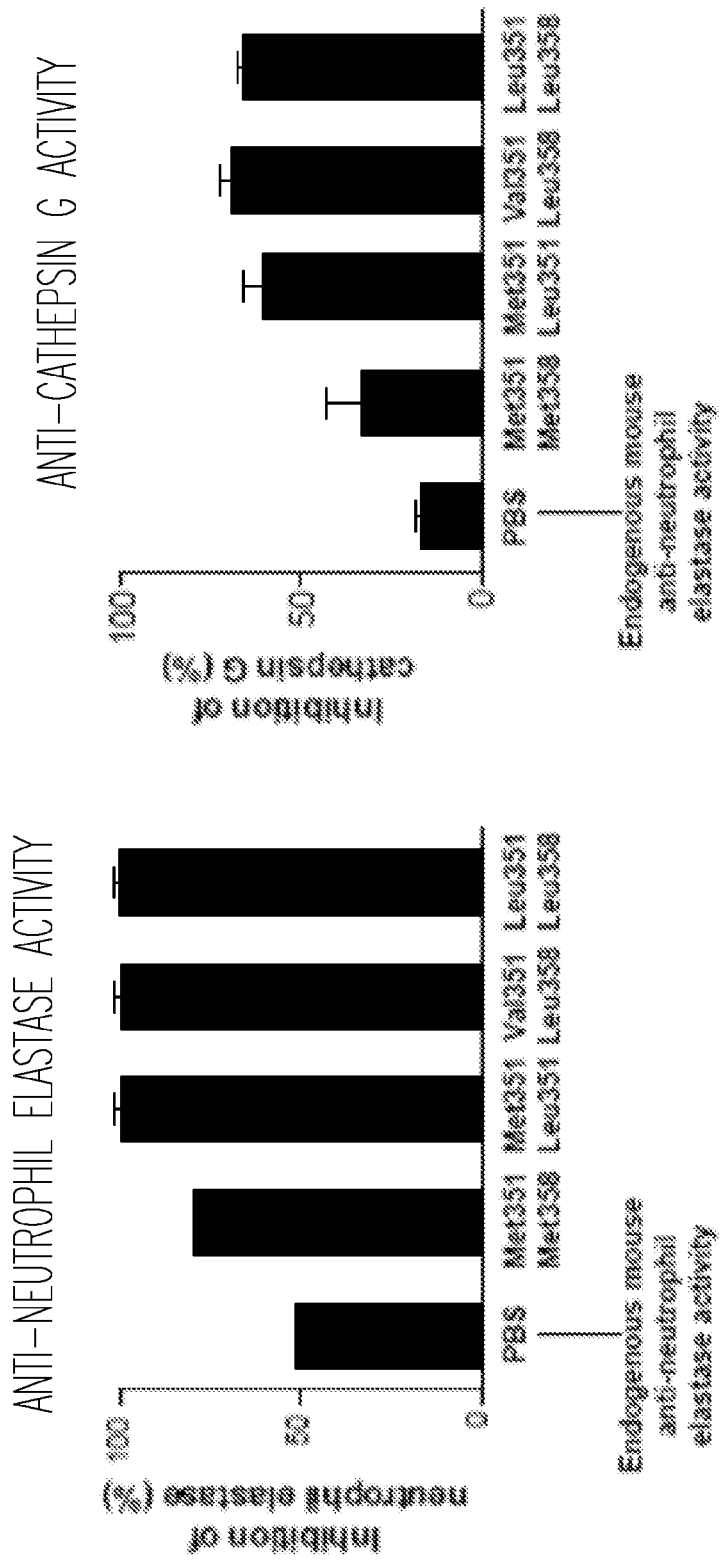
FIG. 16. Evaluation of serum anti-protease activity in mice infected with AAV8-hAAT oxidation-resistant variants or wild-type AAT (oxidation-sensitive).
Figure 17:
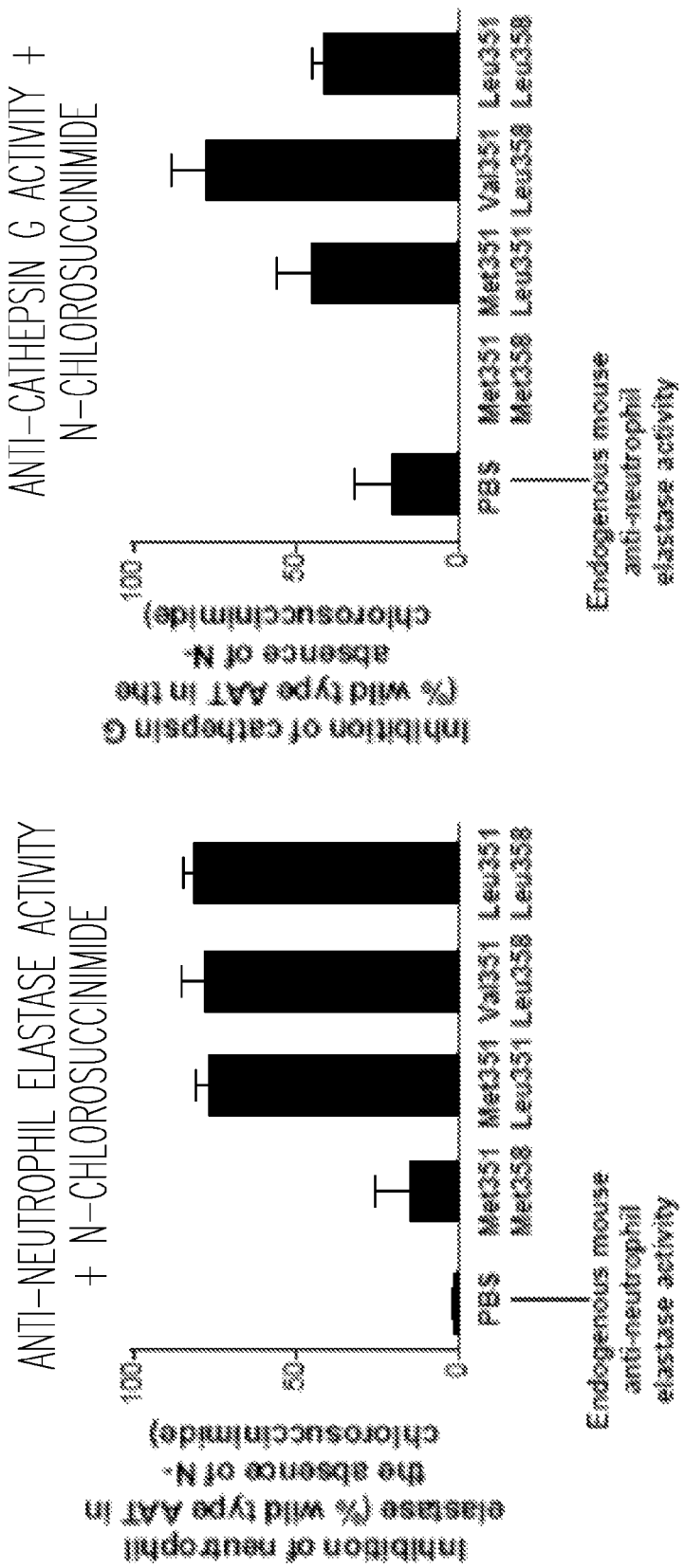
FIG. 17. Evaluation of serum anti-protease activity in the presence of oxidant stress in serum from in mice infected with AAV8-hAAT variants or wild-type AAT.

For AAV.vAAT the process uses a two plasmid transfection system in adherent HEK293 cells from highly characterized and qualified cell bank that meets regulatory expectations. Plasmids are kanamycin resistant for selection and compatible with FDA guidelines for manufacturing clinical grade drug. After 5 days, cells are harvested and a crude viral lysate is made by freeze/thaw cycles followed by benzonase digestion to digest host cell derived nucleic acids followed by high salt to quench benzonase and disrupt AAV-cell membrane interactions. The resulting cell harvest is clarified by depth filtration, concentrated by tangential flow filtration (TFF) followed by two steps of membrane ion exchange, buffer exchange on TFF and separation of empty from full capsids by BIA monolith column (FIG. 9). All steps are scalable and transferable to contract manufacturing for eventual large scale production. The methods, translated to GMP through SUPS and batch records will be perfected via multiple mock productions under GMP conditions with the specific AAV.vAAT transgene. Staff audits the documents to assess process yield and quality. Lots are released based on criteria agreed to by the FDA for clinical development of AAV vectors for clinical application, and include: (1) testing of the crude viral lysate for mycoplasma and on 11 different viruses; (2) testing of the bulk product for transgene function and product, viral capsid purity, genome structure stability, empty capsids, infectious titer, viral titer, and replication competent AAV; and (3) testing of the final product lot for sterility, endotoxin, pH, appearance, and viral titer.

Phase 1 Trial.

A clinical phase I study compares 3 doses, $8 \times 10^{12}$, $8 \times 10^{13}$ and $4 \times 10^{14}$ genome copies administered by the intrapleural route to individuals (n=5 each dose) with a ZZ or Z Null genotype and serum AAT levels <11 µM. Besides the normal safety parameters, the goal of the therapy is to reach a sustained concentration of >1.2 µM AAT in ELF, the lung "protective level"[164]. The completion of this study provides critical safety and preliminary efficacy data. Most of the parameters in the phase I trial utilize standard clinical assays available in all academic medical hospitals. However, there are also assays relevant to AAV.vAAT function administered to AAT deficient patients, and assays to assess immune response to AAV.vAAT.

REFERENCES

1. Johnson D Travis J. The oxidative inactivation of human alpha-1-proteinase inhibitor. Further evidence for methionine at the reactive center. J Biol Chem 1979; 254:4022-4026
2. De B, Heguy A, Leopold P L, Wasif N, Korst R J, Hackett N R, Crystal R G. Intrapleural administration of a serotypes adeno-associated virus coding for alpha1-antitrypsin mediates persistent, high lung and serum levels of alpha1-antitrypsin. Mol Ther 2004; 10:1003-1010
3. Pagovich O E, Wang B, Chiuchiolo M J, Kaminsky S M, Sondhi D, Jose C L, Rice C C, Brooks S F, Mezey J G, Crystal R G. Anti-hIgE gene therapy of peanut-induced anaphylaxis in a humanized murine model of peanut allergy. J Allergy Clin Immunol 2016; 138:1652-1662
4. Brantly M, Nukiw a T, Crystal R G. Molecular basis of alpha-1-antitrypsin deficiency. Am J Med 1988; 84:13-31
5. Brantly M L, Paul L D, Miller B H, Falk R T, Wu M, Crystal R G. Clinical features and history of the destructive lung disease associated with alpha-1-antitrypsin deficiency of adults with pulmonary symptoms. Am Rev Respir Dis 1988; 138:327-336
6. Carrell, R. & Boswell, D. (1986) in *Proteinase Inhibitors*, eds. Barrett, A. & Salvensen, G. (Elsevier, Amsterdam), pp. 403-420.
7. Crystal R G. Alpha 1-antitrypsin deficiency, emphysema, and liver disease. Genetic basis and strategies for therapy. J Clin Invest 1990; 85:1343-1352
8. Gadek J E, Fells G A, Zimmerman R L, Rennard S I, Crystal R G. Antielastases of the human alveolar structures. Implications for the protease-antiprotease theory of emphysema. J Clin Invest 1981; 68:889-898
9. Lungarella G, Cavarra E, Lucattelli M, Martorana P A. The dual role of neutrophil elastase in lung destruction and repair. Int J Biochem Cell Biol 2008; 40:1287-1296
10. Silverman E K Sandhaus R A. Clinical practice. Alpha1-antitrypsin deficiency. N Engl J Med 2009; 360:2749-2757
11. Crystal R G, Brantly M L, Hubbard R C, Curiel D T, States D J, Holmes M D. The alpha 1-antitrypsin gene and its mutations. Clinical consequences and strategies for therapy. Chest 1989; 95:196-208
12. Tuder R M, Janciauskiene S M, Petrache I. Lung disease associated with alpha1-antitrypsin deficiency. Proc Am Thorac Soc 2010; 7:381-386
13. Gadek J E, Klein H G, Holland P V, Crystal R G. Replacement therapy of alpha 1-antitrypsin deficiency. Reversal of protease-antiprotease imbalance within the alveolar structures of PIZ subjects. J Clin Invest 1981; 68:1158-1165
14. Wewers M D, Casolaro M A, Sellers S E, Swayze S C, McPhaul K M, Wittes J T, Crystal R G. Replacement therapy for alpha 1-antitrypsin deficiency associated with emphysema. N Engl J Med 1987; 316:1055-1062
15. Chapman K R, Burdon J G, Piitulainen E, Sandhaus R A, Seersholm N, Stocks J M, Stoel B C, Huang L, Yao Z, Edelman J M, McElvaney N G. Intravenous augmentation treatment and lung density in severe alpha1 antitrypsin deficiency (RAPID): a randomised, double-blind, placebo-controlled trial. Lancet 2015; 386:360-368 Crystal R G. Augmentation treatment for alpha1 antitrypsin deficiency. Lancet 2015; 386:318-320
17. Crystal R G. Compelling evidence for the efficacy of alpha1-antitrypsin augmentation treatment for alpha1-antitrypsin deficiency. Lancet Respir Med 2017; 5:7-8
18. McElvaney N G, Burdon J, Holmes M, Glanville A, Wark P A, Thompson P J, Hernandez P, Chlumsky J, Teschler H, Ficker J H, Seersholm N, Altraja A, Makitaro R, Chorostowska-Wynimko J, Sanak M, Stoicescu P I, Piitulainen E, Vit O, Wencker M, Tortorici M A, Fries M, Edelman J M, Chapman K R, Rapid Extension Trial Group. Long-term efficacy and safety of alpha1 proteinase inhibitor treatment for emphysema caused by severe alpha1 antitrypsin deficiency: an open-label extension trial (RAPID-OLE). Lancet Respir Med 2017; 5:51-60
19. Chiuchiolo M J, Kaminsky S M, Sondhi D, Hackett N R, Rosenberg J B, Frenk E Z, Hwang Y, Van de Graaf B G, Hutt J A, Wang G, Benson J, Crystal R G. Intrapleural administration of an AAVrh.10 vector coding for human alpha1-antitrypsin for the treatment of alpha1-antitrypsin deficiency. Hum Gene Ther Clin Dev 2013; 24:161-173
20. Chulay J D, Ye G J, Thomas D L, Knop D R, Benson J M, Hutt J A, Wang G, Humphries M, Flotte T R. Preclinical evaluation of a recombinant adeno-associated virus vector expressing human alpha-1 antitrypsin made using a recombinant herpes simplex virus production method. Hum Gene Ther 2011; 22:155-165
21. Conlon T J, Cossette T, Erger K, Choi Y K, Clarke T, Scott-Jorgensen M, Song S, Campbell-Thompson M, Craw ford J, Flotte T R. Efficient hepatic delivery and expression from a recombinant adeno-associated virus 8 pseudotyped alpha1-antitrypsin vector. Mol Ther 2005; 12:867-875
22. De B P, Heguy A, Hackett N R, Ferris B, Leopold P L, Lee J, Ferre L, Gao G, Wilson J M, Crystal R G. High levels of persistent expression of alpha1-antitrypsin mediated by the nonhuman primate serotype rh.10 adeno-associated virus despite preexisting immunity to common human adeno-associated viruses. Mol Ther 2006; 13:67-76
23. Flotte T R, Conlon T J, Poirier A, Campbell-Thompson M, Byrne B J. Preclinical characterization of a recombinant adeno-associated virus type 1-pseudotyped vector demonstrates dose-dependent injection site inflammation and dissemination of vector genomes to distant sites. Hum Gene Ther 2007; 18:245-256

24. Halbert C L, Madtes D K, Vaughan A E, Wang Z, Storb R, Tapscott S J, Miller A D. Expression of human alpha1-antitrypsin in mice and dogs following AAV6 vector-mediated gene transfer to the lungs. Mol Ther 2010; 18:1165-1172
25. Limberis M P Wilson J M. Adeno-associated virus serotype 9 vectors transduce murine alveolar and nasal epithelia and can be readministered. Proc Natl Acad Sci USA 2006; 103:12993-12998
26. Limberis M P, Vandenberghe L H, Zhang L, Pickles R J, Wilson J M. Transduction efficiencies of novel AAV vectors in mouse airway epithelium in vivo and human ciliated airway epithelium in vitro. Mol Ther 2009; 17:294-301
27. Lu Y, Choi Y K, Campbell-Thompson M, Li C, Tang O, Crawford J M, Flotte T R, Song S. Therapeutic level of functional human alpha 1 antitrypsin (hAAT) secreted from murine muscle transduced by adeno-associated virus (rAAV1) vector. J Gene Med 2006; 8:730-735
28. Song S, Morgan M, Ellis T, Poirier A, Chesnut K, Wang J, Brantly M, Muzyczka N, Byrne B J, Atkinson M, Flotte T R. Sustained secretion of human alpha-1-antitrypsin from murine muscle transduced with adeno-associated virus vectors. Proc Natl Acad Sci USA 1998; 95:14384-14388
29. Song S, Embury J, Laipis P J, Berns K I, Crawford J M, Flotte T R. Stable therapeutic serum levels of human alpha-1 antitrypsin (AAT) after portal vein injection of recombinant adeno-associated virus (rAAV) vectors. Gene Ther 2001; 8:1299-1306
30. Virella-Lowell I, Zusman B, Foust K, Loiler 5, Conlon T, Song S, Chesnut K A, Ferkol T, Flotte T R. Enhancing rAAV vector expression in the lung. J Gene Med 2005; 7:842-850
31. Xiao W, Berta S C, Lu M M, Moscioni A D, Tazelaar J, Wilson J M. Adeno-associated virus as a vector for liver-directed gene therapy. J Virol 1998; 72:10222-10226
32. Beatty K, Bieth J, Travis J. Kinetics of association of serine proteinases with native and oxidized alpha-1-proteinase inhibitor and alpha-1-antichymotrypsin. J Biol Chem 1980; 255:3931-3934
33. Carp H Janoff A. Potential mediator of inflammation. Phagocyte-derived oxidants suppress the elastase-inhibitory capacity of alpha 1-proteinase inhibitor in vitro. J Clin Invest 1980; 66:987-995
34. Cohen A B James H L. Reduction of the elastase inhibitory capacity of alpha 1-antitrypsin by peroxides in cigarette smoke: an analysis of brands and filters. Am Rev Respir Dis 1982; 126:
35. Evans M D Pryor W A. Cigarette smoking, emphysema, and damage to alpha 1-proteinase inhibitor. Am J Physiol 1994; 266:L593-L611
36. Matheson N R, Wong P S, Travis J. Enzymatic inactivation of human alpha-1-proteinase inhibitor by neutrophil myeloperoxidase. Biochem Biophys Res Commun 1979; 88:402-409
37. Scott L J, Russell G I, Nixon N B, Dawes P T, Mattey D L. Oxidation of alpha1-proteinase inhibitor by the myeloperoxidase-hydrogen peroxidase system promotes binding to immunoglobulin A. Biochem Biophys Res Commun 1999; 255:562-567
38. Summers F A, Morgan P E, Davies M J, Hawkins C L. Identification of plasma proteins that are susceptible to thiol oxidation by hypochlorous acid and N-chloramines. Chem Res Toxicol 2008; 21:1832-1840
39. Taggart C, Cervantes-Laurean D, Kim G, McElvaney N G, Wehr N, Moss J, Levine R L. Oxidation of either methionine 351 or methionine 358 in alpha 1-antitrypsin causes loss of anti-neutrophil elastase activity. J Biol Chem 2000; 275:27258-27265
40. Elliott P R, Lomas D A, Carrell R W, Abrahams J P. Inhibitory conformation of the reactive loop of alpha 1-antitrypsin. Nat Struct Biol 1996; 3:676-681
41. Janoff A, Carp H, Lee D K, Drew R T. Cigarette smoke inhalation decreases alpha 1-antitrypsin activity in rat lung. Science 1979; 206:1313-1314
42. Courtney M, Jallat S, Tessier L H, Benavente A, Crystal R G, LeCocq J P. Synthesis in E. coli of alpha 1-antitrypsin variants of therapeutic potential for emphysema and thrombosis. Nature 1985; 313:149-151
43. Jallat S, Tessier L H, Benavente A, Crystal R G, Courtney M. Antiprotease targeting: altered specificity of alpha 1-antitrypsin by amino acid replacement at the reactive centre. Rev Fr Transfus Immunohematol 1986; 29:287-298
44. Straus S D, Fells G A, Wewers M D, Courtney M, Tessier L H, Tolstoshev P, LeCocq J P, Crystal R G. Evaluation of recombinant DNA-directed E. coli produced alpha 1-antitrypsin as an anti-neutrophil elastase for potential use as replacement therapy of alpha 1-antitrypsin deficiency. Biochem Biophys Res Commun 1985; 130:1177-1184
45. Duranton J Bieth J G. Inhibition of proteinase 3 by [alpha]1-antitrypsin in vitro predicts very fast inhibition in vivo. Am J Respir Cell Mol Biol 2003; 29:57-61
46. Spencer L T, Paone G, Krein P M, Rouhani F N, Rivera-Nieves J, Brantly M L. Role of human neutrophil peptides in lung inflammation associated with alpha1-antitrypsin deficiency. Am J Physiol Lung Cell Mol Physiol 2004; 286:L514-L520
47. Petrache I, Fijalkowska I, Medler T R, Skirball J, Cruz P, Zhen L, Petrache H I, Flotte T R, Tuder R M. a-1 Antitrypsin Inhibits Caspase-3 Activity, Preventing Lung Endothelial Cell Apoptosis. Am J Pathol 2006; 169:1155-1166
48. Janciauskiene S M, Nita I M, Stevens T. Alpha1-antitrypsin, old dog, new tricks. Alpha1-antitrypsin exerts in vitro anti-inflammatory activity in human monocytes by elevating cAMP. J Biol Chem 2007; 282:8573-8582
49. Bergin D A, Reeves E P, Meleady P, Henry M, McElvaney O J, Carroll T P, Condron C, Chotirmall S H, Clynes M, O'Neill S J, McElvaney N G. alpha-1 Antitrypsin regulates human neutrophil chemotaxis induced by soluble immune complexes and IL-8. J Clin Invest 2010; 120:4236-4250
50. Shahaf G, Moser H, Ozeri E, Mizrahi M, Abecassis A, Lewis E C. alpha-1-antitrypsin gene delivery reduces inflammation, increases T-regulatory cell population size and prevents islet allograft rejection. Mol Med 2011; 17:1000-1011
51. Lewis E C. Expanding the clinical indications for alpha(1)-antitrypsin therapy. Mol Med 2012; 18:957-970
52. Jonigk D, Al-Omari M, Maegel L, Muller M, Izykowski N, Hong J, Hong K, Kim S H, Dorsch M, Mahadeva R, Laenger F, Kreipe H, Braun A, Shahaf G, Lewis E C, Welte T, Dinarello C A, Janciauskiene S. Anti-inflammatory and immunomodulatory properties of alpha1-antitrypsin without inhibition of elastase. Proc Natl Aced Sci USA 2013; 110:15007-15012
53. Bergin D A, Reeves E P, Hurley K, Wolfe R, Jameel R, Fitzgerald S, McElvaney N G. The circulating proteinase inhibitor alpha-1 antitrypsin regulates neutrophil degranulation and autoimmunity. Sci Transl Med 2014; 6:217ra1
54. Ehlers M R. Immune-modulating effects of alpha-1 antitrypsin. Biol Chem 2014; 395:1187-1193

55. Geraghty P, Eden E, Piilai M, Campos M, McElvaney N G, Foronjy R F. alpha1-Antitrypsin activates protein phosphatase 2A to counter lung inflammatory responses. Am J Respir Crit Care Med 2014; 190:1229-1242

56. Guyot N, Wartelle J, Malleret L, Todorov A A, Devouassoux G, Pacheco Y, Jenne D E, Belaaouaj A. Unopposed cathepsin G, neutrophil elastase, and proteinase 3 cause severe lung damage and emphysema. Am J Pathol 2014; 184:2197-2100

57. Kaner Z, Ochayon D E, Shahaf G, Baranovski B M, Bahar N, Mizrahi M, Lewis E C. Acute Phase Protein alpha1-Antitrypsin Reduces the Bacterial Burden in Mice by Selective Modulation of Innate Cell Responses. J Infect Dis 2015; 211:1489-1498

58. Sinden N J, Baker M J, Smith D J, Kreft J U, Dafforn T R, Stockley R A. alpha-1-antitrypsin variants and the proteinase/antiproteinase imbalance in chronic obstructive pulmonary disease. Am J Physiol Lung Cell Mol Physiol 2015; 308:L179-L190

59. Alam S, Li Z, Janciauskiene S, Mahadeva R. Oxidation of Z alpha1-antitrypsin by cigarette smoke induces polymerization: a novel mechanism of early-onset emphysema. Am J Respir Cell Mol Biol 2011; 45:261-269

60. Lockett A D, Van Demark M, Gu Y, Schweitzer K S, Sigua N, Kamocki K, Fijalkowska Garrison J, Fisher A J, Serban K, Wise R A, Flotte T R, Mueller C, Presson R G, Jr., Petrache H I, Tuder R M, Petrache I. Effect of cigarette smoke exposure and structural modifications on the alpha-1 Antitrypsin interaction with caspases. Mol Med 2012; 18:445-454

61. Alam S, Li Z, Atkinson C, Jonigk D, Janciauskiene S, Mahadeva R. Z alpha1-antitrypsin confers a proinflammatory phenotype that contributes to chronic obstructive pulmonary disease. Am J Respir Crit Care Med 2014; 189:909-931

62. The Alpha-1-Antitrypsin Deficiency Registry Study Group. Survival and FEV1 decline in individuals with severe deficiency of alpha1-antitrypsin. The Alpha-1-Antitrypsin Deficiency Registry Study Group. Am J Respir Crit Care Med 1998; 158:49-59

63. Lomas D A Parfrey H. Alpha1-antitrypsin deficiency. 4: Molecular pathophysiology. Thorax 2004; 59:529-535

64. Tanash H A, Nilsson P M, Nilsson J A, Piitulainen E Survival in severe alpha-1-antitrypsin deficiency (RZZ). Respir Res 2010; 11:44

65. de Serres F J Blanco I. Prevalence of alpha1-antitrypsin deficiency alleles PI*S and PI*Z worldwide and effective screening for each of the five phenotypic classes PI*MS, PI*MZ, PI*SS, PI*SZ, and PI*ZZ: a comprehensive review. Ther Adv Respir Dis 2012; 6:277-295

66. Perlmutter D H Silverman G A. Hepatic fibrosis and carcinogenesis in alpha1-antitrypsin deficiency: a prototype for chronic tissue damage in gain-of-function disorders. Cold Spring Herb Perspect Biol 2011; 3:a005801

67. Topic A, Ljujic M, Radojkovic D. Alpha-1-antitrypsin in pathogenesis of hepatocellular carcinoma. Hepat Mon 2012; 12:e7042

68. Inaty H Arabelovic S. alpha1-Antitrypsin deficiency in a patient diagnosed with granulomatosis with polyangiitis. BMJ Case Rep 2013; 2013:doi:10.1136/bcr-2013-009045

69. Teckman J H. Liver disease in alpha-1 antitrypsin deficiency: current understanding and future therapy. Copd 2013; 10 Suppl 1:35-43

70. Alberici F, Martorana D, Vaglio A. Genetic aspects of anti-neutrophil cytoplasmic antibody-associated vasculitis. Nephrol Dial Transplant 2014; 30 (suppl 1):i37-i45

71. de Serres F Blanco I. Role of alpha-1 antitrypsin in human health and disease. J Intern Med 2014; 276:311-335

72. Stone H, Pye A, Stockley R A. Disease associations in alpha-1-antitrypsin deficiency. Respir Med 2014; 108:338-343

73. Duvoix A, Roussel B D, Lomas D A. Molecular pathogenesis of alpha-1-antitrypsin deficiency. Rev Mal Respir 2014; 31:992-1002

74. Greene C M, Miller S D, Carroll T, McLean C, O'Mahony M, Lawless M W, O'Neill S J, Taggart C C, McElvaney N G. Alpha-1 antitrypsin deficiency: a conformational disease associated with lung and liver manifestations. J Inherit Metab Dis 2008; 31:21-34

75. Mornex J F, Chytil-Weir A, Martinet Y, Courtney M, LeCocq J P, Crystal R G. Expression of the alpha-1-antitrypsin gene in mononuclear phagocytes of normal and alpha-1-antitrypsin-deficient individuals. J Clin Invest 1986; 77:1952-1961

76. van't Wout E F, van Schadewijk A, Savage N D, Stolk J, Hiemstra P S. alpha1-antitrypsin production by proinflammatory and antiinflammatory macrophages and dendritic cells. Am J Respir Cell Mol Biol 2012; 46:365-376

77. du Bois R M, Bernaudin J F, Paakko P, Hubbard R, Takahashi H, Ferrans V, Crystal R G. Human neutrophils express the alpha 1-antitrypsin gene and produce alpha 1-antitrypsin. Blood 1991; 77:2724-2730

78. Venembre P, Boutten A, Seta N, Dehoux M S, Crestani B, Aubier M, Durand G. Secretion of alpha 1-antitrypsin by alveolar epithelial cells. FEBS Lett 1994; 346:171-174

79. Cichy J, Potempa J, Travis J. Biosynthesis of alpha1-proteinase inhibitor by human lung-derived epithelial cells. J Biol Chem 1997; 272:8250-8255

80. Geboes K, Ray M B, Rutgeerts P, Callea F, Desmet V J, Vantrappen G. Morphological identification of alpha-l-antitrypsin in the human small intestine. Histopathology 1982; 6:55-60

81. Perlmutter D H, Daniels J D, Auerbach H S, De Schryver-Kecskemeti K, Winter H S, Alpers D H. The alpha 1-antitrypsin gene is expressed in a human intestinal epithelial cell line. J Biol Chem 1989; 264:9485-9490

82. Cox D W, Markovic V D, Teshima I E Genes for immunoglobulin heavy chains and for alpha 1-antitrypsin are localized to specific regions of chromosome 14q. Nature 1982; 297:428-430

83. Schroeder W T, Miller M F, Woo S L, Saunders G F. Chromosomal localization of the human alpha 1-antitrypsin gene (PI) to 14q31-32. Am J Hum Genet 1985; 37:868-872

84. Laurell C-B Eriksson S. The electrophoretic alpha1-globulin pattern of serum in alpha1-antitrypsin deficiency. Scand J Clin Lab Invest 1963; 15:132-140

85. Seixas S, Garcia O, Trovoada M J, Santos M T; Amorim A, Rocha J. Patterns of haplotype diversity within the serpin gene cluster at 14832.1: insights into the natural history of the alpha1-antitrypsin polymorphism. Hum Genet 2001; 108:20-30

86. Stoller J K Aboussouan L S. A review of alpha1-antitrypsin deficiency. Am J Respir Crit Care Med 2012; 185:246-259

87. Kurachi K, Chandra T, Degen S J, White T T, Marchioro T L, Woo S L, Davie E W. Cloning and sequence of cDNA coding for alpha 1-antitrypsin. Proc Natl Acad Sci USA 1981; 78:6826-6830

88. Jeppsson J O. Amino acid substitution Glu leads to Lys alpha1-antitrypsin PiZ. FEBS Lett 1976; 65:195-197

89. Birrer P, McEvaney N G, Chang-Stroman L M, Crystal R G. Alpha 1-antitrypsin deficiency and liver disease. J Inherit Metab Dis 1991; 14:512-525
90. Gooptu B Lomas D A. Conformational pathology of the serpins: themes, variations, and therapeutic strategies. Annu Rev Biochem 2009; 78:147-176
91. Lomas D A, Evans D L, Finch J T, Carrell R W. The mechanism of Z alpha 1-antitrypsin accumulation in the liver. Nature 1992; 357:605-607
92. Nukiwa T, Satoh K, Brantly M L, Ogushi F, Fells G A, Courtney M, Crystal R G. Identification of a second mutation in the protein-coding sequence of the Z type alpha 1-antitrypsin gene. J Biol Chem 1986; 261:15989-15994
93. Long G L, Chandra T, Woo S L, Davie E W, Kurachi K. Complete sequence of the cDNA for human alpha 1-antitrypsin and the gene for the S variant. Biochemistry 1984; 23:4828-4837
94. Owen M C, Carrell R W, Brennan S O. The abnormality of the S variant of human alpha-1-antitrypsin. Biochim Biophys Acta 1976; 453:257-261
95. Yoshida A, Ewing C, Wessels M, Lieberman J, Gaidulis L. Molecular abnormality of PI S variant of human alpha1-antitrypsin. Am J Hum Genet 1977; 29:233-239
96. Ogushi F, Hubbard R C, Fells G A, Casolaro M A, Curiel D T, Brantly M L, Crystal R G. Evaluation of the S-type of alpha-1-antitrypsin as an in vivo and in vitro inhibitor of neutrophil elastase. Am Rev Respir Dis 1988; 137: 364-370
97. Bornhorst J A, Greene D N, Ashwood E R, Grenache D G. alpha1-Antitrypsin phenotypes and associated serum protein concentrations in a large clinical population. Chest 2013; 143:1000-1008
98. FDA, B. P. A. C. (2017).
99. American Thoracic S European Respiratory S. American Thoracic Society/European Respiratory Society statement: standards for the diagnosis and management of individuals with alpha-1 antitrypsin deficiency. Am J Respir Crit Care Med 2003; 168:818-900
100. Thompson Healthcare (2010) *Red Book: pharmacy's fundamental reference* (Thomson Reuters: PDR Network.
101. Bernstein J A, Alexis N, Barnes C, Bernstein I L, Bernstein J A, Nel A, Peden D, Diaz-Sanchez D, Tarlo S M, Williams P B. Health effects of air pollution. J Allergy Clin Immunol 2004; 114:1116-1123
102. Ciencewicki J, Trivedi S, Kleeberger S R. Oxidants and the pathogenesis of lung diseases. J Allergy Clin Immunol 2008; 122:456-468
103. Chiuchiolo M J Crystal R G. Gene Therapy for Alpha-1 Antitrypsin Deficiency Lung Disease, Ann Am Thorac Soc 2016; 13 Suppl 4:S352-5369
104. Garver R I, Jr., Chytil A, Courtney M, Crystal R G. Clonal gene therapy: transplanted mouse fibroblast clones express human alpha 1-antitrypsin gene in vivo. Science 1987; 237:762-764
105. Rosenfeld M A, Siegfried W, Yoshimura K, Yoneyama K, Fukayama M, Stier L E, Paakko P K, Gilardi P, Stratford-Perricaudet L D, Perricaudet M, Jallat S, Pavirani A, Lecocq J-P, Crystal R G. Adenovirus-mediated transfer of a recombinant alpha 1-antitrypsin gene to the lung epithelium in vivo. Science 1991; 252:431-434
106. Daya S Berns K I. Gene therapy using adeno-associated virus vectors. Clin Microbial Rev 2008; 21:583-593
107. Gao G, Vandenberghe L H, Alvira M R, Lu Y, Calcedo R, Zhou X, Wilson J M. Clades of adeno-associated viruses are widely disseminated in human tissues. J Virol 2004; 78:6381-6388
108. Asokan A, Schaffer D V, Jude S R. The AAV Vector Toolkit: Poised at the Clinical Crossroads. Mol Ther 2012; 20:699-708
109. Niwa H, Yamamura K, Miyazaki J. Efficient selection for high-expression transfectants with a novel eukaryotic vector. Gene 1991; 108:193-199
110. Carrell R, Owen M, Brennan S, Vaughan L. Carboxy terminal fragment of human alpha-1-antitrypsin from hydroxylamine cleavage: homology with antithrombin III. Biochem Biophys Res Commun 1979; 91:1032-1037
111. Carrell R W, Jeppsson J O, Laurell C B, Brennan S O, Owen M C, Vaughan L, Boswell D R. Structure and variation of human alpha 1-antitrypsin. Nature 1982; 298:329-334
112. Loebermann H, Tokuoka R, Deisenhofer J, Huber R. Human alpha 1-proteinase inhibitor. Crystal structure analysis of two crystal modifications, molecular model and preliminary analysis of the implications for function. J Mol Biol 1984; 177:531-557
113. Buhl R, Meyer A, Vogelmeier C. Oxidant-protease interaction in the lung. Prospects for antioxidant therapy. Chest 1996; 110:267S-272S
114. Topic, A. & Radojkovic, D. (2012), ed. Irusen, E. M. (InTech, p. http://www.intechopen.com/books/lung-diseases-selected-state-of-the-art-reviews/polymerization-and-oxidation-of-alpha-1-antitrypsin-in-pathogenesis-of-emphysema.
115. Li Z, Alam S, Wang J, Sandstrom C S, Janciauskiene S, Mahadeva R. Oxidized {alpha}1-antitrypsin stimulates the release of monocyte chemotactic protein-1 from lung epithelial cells: potential role in emphysema. Am J Physiol Lung Cell Mol Physiol 2009; 297:L388-L400
116. Moraga F Janciauskiene S. Activation of primary human monocytes by the oxidized form of alpha1-antitrypsin. J Biol Chem 2000; 275:7693-7700
117. Ueda M, Mashiba S, Uchida K. Evaluation of oxidized alpha-1-antitrypsin in blood as an oxidative stress marker using anti-oxidative alpha1-AT monoclonal antibody. Clin Chim Acta 2002; 317:125-131
118. Rosenberg S, Barr P J, Najarian R C, Hallewell R A. Synthesis in yeast of a functional oxidation-resistant mutant of human alpha-antitrypsin. Nature 1984; 312:77-80
119. Nukiw a, T., Ogushi, F., & Crystal, R. G. (1996) in Alpha 1-antitrypsin deficiency, ed. Crystal, R. G. (Marcel Dekker, Inc., New York), pp. 33-43.
120. Elliott P R, Pei X Y, Dafforn T R, Lomas D A. Topography of a 2.0 A structure of alpha1-antitrypsin reveals targets for rational drug design to prevent conformational disease. Protein Sci 2000; 9:1274-1281
121. Gadek J E, Fells G A, Crystal R G. Cigarette smoking induces functional antiprotease deficiency in the lower respiratory tract of humans. Science 1979; 206:1315-1316
122. Bals R, Xiao W, Sang N, Weiner D J, Meegalla R L, Wilson J M. Transduction of well-differentiated airway epithelium by recombinant adeno-associated virus is limited by vector entry. J Virol 1999; 73:6085-6088
123. Yang Y, Li Q, Ertl H C, Wilson J M. Cellular and humoral immune responses to viral antigens create barriers to lung-directed gene therapy with recombinant adenoviruses. J Virol 1995; 69:2004-2015
124. Ferrari S, Griesenbach U, Geddes D M, Alton E. Immunological hurdles to lung gene therapy. Clin Exp Immunol 2003; 132:1-8
125. Duan D, Yue Y, Yan Z, McCray P B, Jr., Engelhardt J F. Polarity influences the efficiency of recombinant adeno-associated virus infection in differentiated airway epithelia. Hum Gene Ther 1998; 9:2761-2776
126. Liqun Wang R, McLaughlin T, Cassette T, Tang Q, Faust K, Campbell-Thompson M, Martino A, Cruz P, Loiler S, Mueller C, Flotte T R. Recombinant AAV serotype and capsid mutant comparison for pulmonary gene transfer of alpha-1-antitrypsin using invasive and noninvasive delivery. Mol Ther 2009; 17:81-87
127. Yu H, Buff S M, Baatz J E, Virella-Lowell I. Oral instillation with surfactant phospholipid: a reliable alternative to intratracheal injection in mouse studies. Lab Anim 2008; 42:294-304
128. Song, S., Scott-Jorgensen, M., Wang, J., Poirier, A., Crawford, J., Campbell-Thompson, M., & Flotte, T. R. (2002) United States).
129. Brantly M L, Chulay J D, Wang L, Mueller C, Humphries M, Spencer L T, Rouhani F, Conlon T J, Calcedo R, Betts M R, Spencer C, Byrne B J, Wilson J M, Flotte T R. Sustained transgene expression despite T lymphocyte responses in a clinical trial of rAAV1-AAT gene therapy. Proc Natl Acad Sci USA 2009; 106:16363-16368
130. Flotte T R, Trapnell B C, Humphries M, Carey B, Calcedo R, Rouhani F, Campbell-Thompson M, Yachnis A T, Sandhaus R A, McElvaney N G, Mueller C, Messina L M, Wilson J M, Brantly M, Knop D R, Ye G J, Chulay J D. Phase 2 clinical trial of a recombinant adeno-associated viral vector expressing alpha1-antitrypsin: interim results. Hum Gene Ther 2011; 22:1239-1247
131. Mueller C, Chulay J D, McElvaney N G, Gernoux G, Reeves E P, Rouhani F N, Humphries M, Gruntman A M, Campbell-Thompson M, Wilson J M, Flotte T R. Sustained expression with partial correction of neurtrophil defects 5 years after intramuscular rAAV1 gene therapy for alpha-1 antitrypsin deficiency. Mol Ther 2016; 24:S11-S12
132. Heguy A Crystal R G. Intrapleural 'outside-in' gene therapy: therapeutics for organs of the chest via gene transfer to the pleura. Current opinion in molecular therapeutics 2005; 7:440-453
133. Mae M Crystal R G. Gene transfer to the pleural mesothelium as a strategy to deliver proteins to the lung parenchyma. Hum Gene Ther 2002; 13:1471-1482
134. Finley D J Rusch V W. Anatomy of the pleura. Thorac Surg Clin 2011; 21:157-163
135. Wang N S. Anatomy and physiology of the pleural space. Clin Chest Med 1985; 6:3-16
136. Rennard S I, Jaurand M C, Bignon J, Kawanami O, Ferrans V J, Davidson J, Crystal R G. Role of pleural mesothelial cells in the production of the submesothelial connective tissue matrix of lung. Am Rev Respir Dis 1984; 130:267-274
137. Agostoni E Zocchi L. Pleural liquid and its exchanges. Respir Physiol Neurobiol 2007; 159:311-323
138. Noppen M. Normal volume and cellular contents of pleural fluid. Curr Opin Pulm Med 2001; 7:180-182
139. Mutsaers S E Mesothelial cells: their structure, function and role in serosal repair. Respirology 2002; 7:171-191
140. Noppen M, De Waele M, Li R, Gucht K V, D'Haese J, Gerlo E, Vincken W. Volume and cellular content of normal pleural fluid in humans examined by pleural lavage, Am J Respir Crit Care Med 2000; 162:1023-1026
141. Negrini D Moriondo A. Pleural function and lymphatics. Acta Physiol (Oxf) 2013; 207:244-259
142. Rodriguez-Panadero F Montes-Worboys A. Mechanisms of pleurodesis. Respiration; international review of thoracic diseases 2012; 83:91-98
143. van den Heuvel M M, Smit H J, Barbierato S B, Havenith C E, Beelen R H, Postmus P E. Talc-induced inflammation in the pleural cavity. Eur Respir J 1998; 12:1419-1423
144. Cantin A Crystal R G. Oxidants, antioxidants and the pathogenesis of emphysema. Eur J Respir Dis Suppl 1985; 139:7-17
145. Cross C E, van d, V, O'Neill C A, Louie S, Halliwell B. Oxidants, antioxidants, and respiratory tract lining fluids. Environ Health Perspect 1994; 102 Suppl 10:185-191
146. Wozniak J, Wandtke T, Kopinski P, Chorostowska-Wynimko J. Challenges and Prospects for Alpha-1 Antitrypsin Deficiency Gene Therapy. Hum Gene Ther 2015; 26:709-718
147. Moraga F, Lindgren S, Janciaskiene S. Effects of noninhibitory alpha-1-antitrypsin on primary human monocyte activation in vitro. Arch Biochem Biophys 2001; 386:221-226
148. Landis S C, Amara S G, Asadullah K, Austin C P, Blumenstein R, Bradley E W, Crystal R G, Darnell R B, Ferrante R J, Fillit H, Finkelstein R, Fisher M, Gendelman H E, Golub R M, Goudreau J L, Gross R A, Gubitz A K, Hesterlee S E, Howells D W, Huguenard J, Kelner K, Koroshetz W, Krainc D, Lazic S E, Levine M S, Macleod M R, McCall J M, Moxley R T, III, Narasimhan K, Noble L J, Perrin S, Porter J D, Stew and O, Unger E, Utz U, Silberberg S D. A call for transparent reporting to optimize the predictive value of preclinical research. Nature 2012; 490:187-191
149. Hubbard R C, Ogushi F, Fells G A, Cantin A M, Jallat S, Courtney M, Crystal R G. Oxidants spontaneously released by alveolar macrophages of cigarette smokers can inactivate the active site of alpha 1-antitrypsin, rendering it ineffective as an inhibitor of neutrophil elastase. J Clin Invest 1987; 80:1289-1295
150. Griffiths S W Cooney C L. Relationship between protein structure and methionine oxidation in recombinant human alpha 1-antitrypsin. Biochemistry 2002; 41:6245-6252
151. Brantly M L, Wittes J T, Vogelmeier C F, Hubbard R C, Fells G A, Crystal R G. Use of a highly purified alpha 1-antitrypsin standard to establish ranges for the common normal and deficient alpha 1-antitrypsin phenotypes. Chest 1991; 100:
152. Padrines M, Schneider-Pozzer M, Bieth J G. Inhibition of neutrophil elastase by alpha-1-proteinase inhibitor oxidized by activated neutrophils. Am Rev Respir Dis 1989; 139:783-790
153. Jallat S, Carvallo D, Tessier L H, Roecklin D, Roitsch C, Ogushi F, Crystal R G, Courtney M. Altered specificities of genetically engineered alpha 1 antitrypsin variants. Protein Eng 1986; 1:29-35
154. Travis J, Matheson N R, George P M, Carrell R W. Kinetic studies on the interaction of alpha 1-proteinase inhibitor (Pittsburgh) with trypsin-like serine proteinases. Biol Chem Hoppe Seyler 1986; 367:853-859
155. Boudier C, Laurent P, Bieth J G. Leukoproteinases and pulmonary emphysema: cathepsin G and other chymotrypsin-like proteinases enhance the elastolytic activity of elastase on lung elastin. Adv Exp Med Biol 1984; 167:313-317
156. Adverum Biotechnologies, I. (2016).
157. Mingozzi F High K A. Immune responses to AAV in clinical trials. Curr Gene Ther 2011; 11:321-330
158. Sands; M. S. (2011).

159. van der Laan L J, Wang Y, Tilanus H W, Janssen H L, Pan O. AAV-mediated gene therapy for liver diseases: the prime candidate for clinical application? Expert Opin Biol Ther 2011; 11:315-327
160. Manna C S, Pierce G F, Arruda V R, Glader B, Ragni M, Rasko J J, Ozelo M C, Hoots K, Blatt P, Konkle B, Dake M, Kaye R, Razavi M, Zajko A, Zehnder J, Rustagi P K, Nakai H, Chew A, Leonard D, Wright J F, Lessard R R, Sommer J M, Tigges M, Sabatino D, Luk A, Jiang H, Mingozzi F, Couto L, Ertl H C, High K A, Kay M A. Successful transduction of liver in hemophilia by AAV-Factor IX and limitations imposed by the host immune response. Nat Med 2006; 12:342-347
161. Schnepp B C, Chulay J D, Ye G J, Flotte T R, Trapnell B C, Johnson P R. Recombinant Adeno-Associated Virus Vector Genomes Take the Form of Long-Lived, Transcriptionally Competent Episomes in Human Muscle. Hum Gene Ther 2016; 27:32-42
162. Sondhi D, Peterson D A, Giannaris E L, Sanders C T, Mendez B S, De B, Rostkowski A B, Blanchard B, Bjugstad K, Sladek J R, Jr., Redmond D E, Jr., Leopold P L, Kaminsky S M; Hackett N R, Crystal R G. AAV2-mediated CLN2 gene transfer to rodent and non-human primate brain results in long-term TPP-I expression compatible with therapy for LINCL. Gene Ther 2005; 12:1618-1632
163. Wensky, A. (2017).
164. Chiuchiolo M J, Kaminsky S M, Sondhi D, Mancenido D, Hollmann C, Crystal R G. Phase I/II study of intrapleural administration of a serotype rh.10 replication-deficient adeno-associated virus gene transfer vector expressing the human alpha1-antitrypsin cDNA to individuals with alpha1-antitrypsin deficiency. Hum Gene Ther Clin Dev 2014; 25:112-133
165. Rennard S I, Basset G, Lecossier D, O'Donnell K M, Pinkston P, Martin P G, Crystal R G. Estimation of volume of epithelial lining fluid recovered by lavage using urea as marker of dilution. J Appl Physiol (1985) 1986; 60:532-538
166. Nathwani A C, Tuddenham E G, Rangarajan S, Rosales C, McIntosh J, Linch D C, Chowdary P, Riddell A, Pie A J, Harrington C, O'Beirne J, Smith K, Pasi J, Glader B, Rustagi P, Ng C Y, Kay M A, Zhou J, Spence Y, Morton C L, Allay J, Coleman J, Sleep S, Cunningham J M, Srivastava D, Basner-Tschakarjan E, Mingozzi F, High K A, Gray J T, Reiss U M, Nienhuis A W, Davidoff A M. Adenovirus-associated virus vector-mediated gene transfer in hemophilia B. N Engl J Med 2011; 365:2357-2365
167: Meliani A, Leborgne C, Triffault S, Jeanson-Leh L, Veron P, Mingozzi F. Determination of anti-adeno-associated virus vector neutralizing antibody titer with an in vitro reporter system. Hum Gene Ther Methods 2015; 26:45-53

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method to inhibit cathepsin G and neutrophil elastase under conditions of oxidative damage or oxidative stress in a lung of a mammal having emphysema, COPD, respiratory distress syndrome or fibrotic interstitial lung disease comprising: intravenously administering to the mammal, an amount of an adeno-associated viral gene therapy vector comprising an expression cassette coding for a human oxidation-resistant alpha 1-antitrypsin (AAT) that has a leucine at position 358 and a valine at position 351, wherein expression of the oxidation-resistant AAT from the vector in the lung of the mammal results in inhibition of cathepsin G and neutrophil elastase under conditions of the oxidative damage or stress in the lung as a result of increased levels of the oxidation-resistant AAT in the mammal after administration, and wherein the mammal prior to administration of the vector has serum AAT levels of less than 11 µM.

2. The method of claim 1 wherein the mammal is a human.

3. The method of claim 1 wherein the AAV vector comprises a AAV8 or AAVrh.10 capsid.

4. The method of claim 1 wherein the AAV vector is pseudotyped with AAVrh.10, AAV8, AAV9, AAV5, AAVhu.37, AAVhu.20, AA. Vhu.43, AAVhu. S, AA Vhu.2, or AAV7 capsid.

5. The method of claim 1 wherein the AAV vector is pseudotyped.

6. The method of claim 1 wherein the AAV vector is AAV2, AAV5, AAV7, AAV8, AAV9 or AAVrh.10.

7. The method of claim 1 wherein the alpha 1-antitrypsin has an alanine or a valine at position 213.

8. A method to inhibit cathepsin G and neutrophil elastase under conditions of oxidative damage or oxidative stress in a lung of a mammal having emphysema, COPD, respiratory distress syndrome or fibrotic interstitial lung disease comprising: administering to a pleura of the mammal, an amount of an adeno-associated viral gene therapy vector comprising an expression cassette coding for a human oxidation-resistant alpha 1-antitrypsin (AAT) that has a leucine at position 358 and a valine at position 351, wherein expression of the oxidation-resistant AAT from the vector in the lung of the mammal results in inhibition of cathepsin G and neutrophil elastase under conditions of the oxidative damage or stress in the lung as a result of increased levels of the oxidation-resistant AAT in the mammal after administration, and wherein the mammal prior to administration of the vector has serum AAT levels of less than 11 µM.

9. The method of claim 8 wherein the mammal is a human.

10. The method of claim 9 wherein the human has a genome comprising two Z alleles, a null allele and a Z allele, a null allele and a S allele, a Z allele and a S allele, or two S alleles.

11. The method of claim 8 wherein the AAV vector comprises a AAV8 or AAVrh.10 capsid.

12. The method of claim 8 wherein the AAV vector is pseudotyped with AAVrh.10, AAV8, AAV9, AAV5, AAVhu.37, AAVhu.20, AA. Vhu.43, AAVhu.S, AA Vhu.2, or AAV7 capsid.

13. The method of claim 8 wherein the AAV vector is pseudotyped.

14. The method of claim 8 wherein the AAV vector is AAV2, AAV5, AAV7, AAV8, AAV9 or AAVrh.10.

15. The method of claim 8 wherein the alpha 1-antitrypsin has an alanine or a valine at position 213.

16. The method of claim 8 wherein the mammal has emphysema or COPD.

17. The method of claim 8 wherein the mammal has fibrotic interstitial lung disease.

18. The method of claim 1 wherein the mammal has emphysema or COPD.

19. The method of claim 1 wherein the mammal has fibrotic interstitial lung disease.

* * * * *